US006432986B2

(12) United States Patent
Levin

(10) Patent No.: US 6,432,986 B2
(45) Date of Patent: Aug. 13, 2002

(54) COMPOSITIONS, KITS, AND METHODS FOR INHIBITING CEREBRAL NEUROVASCULAR DISORDERS AND MUSCULAR HEADACHES

(76) Inventor: Bruce H. Levin, One Independence Pl. - No. 501, Philadelphia, PA (US) 19106

(*) Notice: Subject to any disclaimer, the term of this patent is extended or adjusted under 35 U.S.C. 154(b) by 0 days.

(21) Appl. No.: 09/118,615

(22) Filed: Jul. 17, 1998

Related U.S. Application Data
(60) Provisional application No. 60/090,110, filed on Jul. 21, 1997, provisional application No. 60/072,845, filed on Jan. 28, 1998, and provisional application No. 60/084,559, filed on May 6, 1998.

(51) Int. Cl.$^7$ ................. A61K 31/445; A61K 31/47; A61K 31/16; A61K 7/16; A61K 9/68

(52) U.S. Cl. ................. 514/330; 514/310; 514/607; 424/28; 424/49; 424/47

(58) Field of Search .................. 514/310, 887, 514/330; 424/28, 435, 49, 47

(56) References Cited

U.S. PATENT DOCUMENTS

| | | | |
|---|---|---|---|
| 3,105,854 A | 10/1963 | Druey | |
| 3,988,475 A | 10/1976 | Manghisi | |
| 4,138,492 A | 2/1979 | Noverola | |
| 4,147,805 A | 4/1979 | Morrow | |
| 4,163,789 A | 8/1979 | Mauri | |
| 4,562,060 A | * 12/1985 | Broberg et al. ............ | 424/28 |
| 4,585,866 A | 4/1986 | Fozard | |
| 4,886,493 A | 12/1989 | Yee | |
| 5,008,289 A | 4/1991 | Bernstein | |
| 5,527,293 A | 6/1996 | Zamierowski | |
| 5,578,315 A | * 11/1996 | Chien et al. ............ | 424/435 |
| 5,667,799 A | 9/1997 | Caldwell | |
| 5,676,635 A | 10/1997 | Levin | |
| 5,676,691 A | 10/1997 | Friedman | |
| 5,726,187 A | 3/1998 | Gaster | |
| 5,858,410 A | 1/1999 | Muller | |
| 5,939,425 A | 8/1999 | Caruso | |
| 5,964,223 A | 10/1999 | Baran | |
| 6,019,994 A | 2/2000 | Evetts et al. ............ | 424/434 |
| 6,110,937 A | 8/2000 | Loughhead | |

FOREIGN PATENT DOCUMENTS

| | | | |
|---|---|---|---|
| BE | 1 009 851 A | 10/1997 | |
| EP | 0 754 453 A1 * | 7/1996 | ......... A61K/31/165 |
| EP | 0 755 678 A1 | 1/1997 | |
| GB | 2 315 673 A | 2/1998 | |
| WO | WO 95/10276 | 4/1995 | |
| WO | 9510276 * | 4/1995 | |
| WO | WO 96/32109 | 10/1996 | |
| WO | WO 97/15548 | 5/1997 | |
| WO | WO 98/15275 A | 4/1998 | |
| WO | WO 98/38998 | 9/1998 | |
| WO | WO 98/38998 A | 9/1998 | |
| WO | WO 99/32103 | 7/1999 | |

OTHER PUBLICATIONS

Maizels et al, Intranasal Treatment for Lidocaine, JAMA pp. 319–321, Jul. 24, 1996.*
Maizels et al, JAMA, vol. 276 (4), Jul. 24, 1996, pp. 319–321.*
Robbins, Lawrance, Headache, vol. 35 (2). 1994, pp. 83–84.*
Barre, Felix, Headache, vol. 22 (2), 1982, pp. 69–73.*
Leisure et al, Seminars is Anesthesia. vol. 15 (1). Mar. 1996, pp. 1–9.*
1996, Med. Sci. Bull. 19(4):1.
Aberg, 1972, Acta Pharmacol. Toxicol. 31:273–286.
Anthony, 1992, Clin. Neurol. Neurosurg. 94:297–301.
APS, 1978, Br. J. Clin. Pharmac. 6:63–68.
Ariëns, 1991, Eur. J. Clin. Pharmacol. 41(2):89–93.
Ariëns, 1990, Pharmaceutisch Weekblad 125:(22)552–554.
Ariëns, 1990, Schweiz Med. Wochenschr. 120(5) 131–134.
Barth, 1984, Pain S269 (abstract—XP–002068058).
Barré, 1982, Headache 22(2):69–73.
Burm, et al., 1994, Br. J. Clin. Pharmacol. 38:125–129.
Butterworth, et al., 1993, Anesthesiology 79(1):88–95.
Caputi, 1997, Headache 37(3):174–179.
Clark, et al., 1991, J. Chromatog. 553:383–390.
Clarkson, et al., 1985, Anesthesiology 62:396–405.
Courtney, et al., 1988, Biochim. Biophys. Acta 939:163–166.
Dejong, et al., 1981, Reg. Anesth. 6:99–103.
Denson, et al., 1992, Reg. Anesth. 17:311–316.
Du Pen, et al., 1992, Pain 49:293–300.
Fozzard, et al., 1985, Card. Electrophys. Arrhythmias 51–57.
Gristwood, et al., 1994, Exp. Opin. Invest. Drugs 3(11):1209–1212.
Honerjäger, 1986, Basic Res. Cardiol. 81(Suppl.):33–37.
Kuhnert, et al., 1981, Fed. Proc. 40(31):684 Drug Disposition, Abstract 2599.
Lee–Son, et al., 1992, Anesthesiology 77:324–335.

(List continued on next page.)

*Primary Examiner*—Russell Travers
(74) *Attorney, Agent, or Firm*—Akin, Gump, Strauss, Hauer & Feld, L.L.P.

(57) ABSTRACT

Methods, kits, and compositions for inhibiting a cerebral neurovascular disorder or a muscular headache in a human patient are provided. The methods comprise intranasally administering to the patient a pharmaceutical composition comprising a local anesthetic, and preferably a long-acting local anesthetic ingredient. A composition useful for practicing the methods of the invention is described which comprises at least one local anesthetic in a pharmaceutically acceptable carrier, wherein the composition is formulated for intranasal delivery. Cerebral neurovascular disorders include migraine and cluster headache. Muscular headaches include tension headaches and muscle contraction headaches. A kit comprising the composition and an intranasal applicator and a method of systemically delivering a pharmaceutically active agent to an animal are also included in the invention.

24 Claims, 2 Drawing Sheets

OTHER PUBLICATIONS

Luduena, et al., 1970, Heterocyclic Compounds 73(5), Abstract 25314a.
Luduena, et al., 1972, Arch. Int. Pharmacodyn. 200:359–369.
Maciewicz, 1988, Clin. J. Pain 4:11–16.
Mather, 1991, Br. J. Anaesth. 67:239–246.
Mazoit, 1993, Anesth Analg 77:477–482.
Moskowitz, 1993, Neurology 43 (Suppl. 3):S16–S20.
Niesel, 1990, Reg. Anaesth. 13(3):54–56 (abstract only).
Reiz, et al., 1986, Br. J. Anaesth. 58:736–746.
Reynolds, 1995, Int. J. Obst. Anesth. 4:93–108.
Robbins, 1995, Headache 35:83–84.
Rowland, et al., 1995, Clin. Pharmacokin. 83–88.
Rutten, et al., 1992, J. Pharm. Pharmacol. 44:355–358.
Rutten, et al., 1991, Br. J. Anaesth. 67:247–256.
Rutten, et al., 1993, Chirality 5(7):485–491.
Schlepper, 1989, European Heart Journal 10(Suppl):73–80.
Strichartz, 1988, Neural Physiology and Local Anesthetic Action pp. 25–45 In: *Neural Blockade in Clinical Anesthesia and Management of Pain*, J.B. Lippincott.
Testa, et al., 1990, Chirality 2:129–133.
Vanhoutte, et al., 1991, Br. J. Pharmacol. 103:1275–1281.
Valenzuela, et a., 1994, Biophys. J. 66:A205 (abstract only Tu–Pos383).
Wahedi, et al., 1990, Reg. Anaesth. 13(3):66–72 (abstract only).
Wang, et al., 1992, J. Gen. Physiol. 100:1003–1020.
Diamond, 1996, JAMA 276(19):1553.
Gherardini, 1995, Acta Anaesthesiol. Scand. 39(6):765–768.
Lane, 1996, J. Am. Med. Assoc. 276(19):1553.
Sachs, 1996, J. Am. Med. Assoc.276(19):1553–1554.
Scott, et al., 1989, Anesth. Analg. 69(5):563–569 (abstract only).
Tulchinsky, 1996, J. Am. Med. Assoc.276(19):1554.
Maizels, 1996, J. Am. Med. Assoc.276(19):1554.
Maizels, et al., 1996, J. Am. Med. Assoc.276(4):319–321.
Markham, et al., 1996, Drugs 52(3):429–449 (abstract only).
Maizels et al., "Intranasal Lidocaine for Treatment of Migraine: A Randomized, Double–blind, Controlled Trial," *Jama*, 276(4):319–321 (Jul. 24–31, 1996).
Kudrow et al., "Rapid and Sustained Relief of Migraine Attacks with Intranasal Lidocaine: Preliminary Findings," *Headache*, 35(2):79–82 (Feb. 1995).
Kittrelle et al., "Cluster Headache—Local Anesthetic Abortive Agents," *Arch. Neurol.*, 42(5):496–498 (May 1985).
Cronen et al., "Cervical Steroid Epidural Nerve Blocks in the Palliation of Pain Secondary to Intrqactable Tension–type Headaches," *Journal of Pain and Symptom Management*, 5(6):379–381 (Dec. 1990).
Barth et al., "Effects of Application of Intravenous Infusion with Local Anesthesia on Chronic Pain Syndromes Especially Headache and Migraine," 4th World Congress on Pain, Seattle, WA, Aug. 31–Sep. 5, 1984, ISSN: 0304–3959, XP002086205, *Pain O* (Suppl. 2):S269 (1984).
Smith et al., "Anesthetizing Migrainous Scalps," Thirteenth Annual Meeting of the American Association for the Study of Headache, San Francisco, CA, Jun. 18–19, 1988, ISSN:0017–8748, XP002086206, *Headache*, 28(4):303 (1988).

* cited by examiner

COMPOSITIONS, KITS, AND METHODS FOR INHIBITING CEREBRAL NEUROVASCULAR DISORDERS AND MUSCULAR HEADACHES

CROSS-REFERENCE TO RELATED APPLICATIONS

This application is entitled to priority pursuant to 35 U.S.C. § 119(e) to U.S. application Ser. No. 08/897,192, filed Jul. 21, 1997, converted to U.S. Provisional Application No. 60/090,110 filed Jul. 21, 1997, U.S. Provisional Application No. 60/072,845, filed Jan. 28, 1998, and U.S. Provisional Application No. 60/084,559, filed May 6, 1998.

FIELD OF THE INVENTION

This invention relates to compositions, kits, and methods for inhibiting muscular headaches and cerebral neurovascular disorders including, but not limited to, neurovascular headaches, migraines, cluster headaches, tinnitus, cerebrovascular spasm, ischemic disorders, and seizures.

BACKGROUND OF THE INVENTION

Headache is a common symptom of numerous diseases and disorders including, but not limited to, migraine, muscle tension, systemic or intracranial infection, intracranial tumor, head injuries, severe hypertension, cerebral hypoxia, certain diseases of the eyes, nose, throat, teeth, and ears, and head pain for which no cause can be determined.

Infrequent headaches can often be determined to result from causes attributable to a particular experience of a patient, such as fatigue, fever, alcohol ingestion, muscle contraction, tension, or the like. The cause of persistent or recurrent headaches is often difficult to determine. Persistent or recurrent headaches include, but are not limited to, muscular headaches, such as tension or muscle contraction headaches, and neurovascular headaches, such as migraines and cluster headaches.

Cerebral neurovascular disorders (CNvDs) are characterized by one or more disturbances in the normal functioning of at least one component of the cerebral vascular or nervous system in a human. CNvDs include, for example, migraine, cluster headaches, other headaches of neurovascular etiology, tinnitus, and cerebrovascular spasm. Human patients afflicted with a CNvD experience a single episode of the disorder, recurrent episodes, persistent episodes, or some combination of these patterns. An individual episode is designated an acute CNvD.

Many CNvDs, such as cerebral vascular accidents, reversible ischemic neurological defects, and transient ischemic attacks (TIA), are associated with functional cerebral ischemia. These are often nonhemorrhagic and of thrombotic, embolic, and vasospastic etiologies. Furthermore, intracranial vasospasm commonly afflicts patients who have experienced an acute cerebral ischemic event such as a stroke and is often problematic following thrombolytic therapy. Numerous symptoms occur during and after acute cerebral ischemic events. Indeed, neurovascular headaches have a vasomotor component to them, which may be responsible for certain or many of the symptoms experienced by patients who are afflicted with prolonged or recurrent neurovascular headaches such as migraines and cluster headaches.

It has been theorized that headaches of neurovascular etiology, such as migraines, for example, result from release of neurotransmitters by trigeminal nerves, which innervate cerebral blood vessels (Moskowitz et al., 1979, Lancet 2:883–885). When disturbed, the trigeminal ganglion is capable of antidromic release of excitatory and other neurotransmitters that initiate sterile inflammation (Demarin et al., 1994, Funct. Neurol. 9:235–245; Moskowitz, 1984, Ann. Neurol. 16:157–168; Moskowitz, 1993, Neurol. 43(Suppl. 3):S16–S20). Studies of trigeminal stimulation, cerebral blood flow, and neuropeptides in animal models and in humans provide support for this theory (Goadsby et al., 1993, Ann. Neurol. 33:48–56; Goadsby et al., 1991, Headache, 31:365–370; Goadsby et al., 1990, Ann. Neurol. 28:183–187; Edvinsson et al., 1994, Cephalalgia 14:88–96). It has been postulated that changes in cerebral blood flow that are triggered by trigeminal stimulation are mediated by the sphenopalatine ganglion (hereinafter, the "SPG") Goadsby et al., 1987, Am J. Physiol. 22:R270–R274; Lambert et al. 1984, J. Neurosurg. 61:307–315; Walters et al., 986, Stroke 17:488–494; Suzuki et al., 1989 Neuroscience 30:595–604).

Another theory posits that nitric oxide is a causative molecule of headaches of neurovascular etiology (Olesen et al., 1995, Cephalalgia 15:94–100). Because the SPG and related postsynaptic and neurovascular structures contain many cells which express nitric oxide synthetase, the SPG mediates the changes in cerebral blood flow that are triggered by trigeminal stimulation, according to this model.

Regardless of whether a neurotransmitter, nitric oxide, both, or neither are the causative agent of headaches of neurovascular etiology, it is clear that the SPG and other dorsonasal nerve structures are key complex structures for targeting the treatment of headaches of neurovascular origin, such treatment including, but not being limited to the treatment of the pain associated with such headaches. Methods of treating headaches of neurovascular etiology which have been described in the prior art have not provided sustained and effective relief from acute neurovascular headache episodes.

Migraine

Migraine is a disorder characterized by persistent headache, which may be severe, which may be associated with visual and gastrointestinal disturbances, and which may also be recurrent. In certain cases, visual changes (designated "aura" by some practitioners) or other symptoms precede the onset of a migraine. Such prodromal symptoms may be due to intracranial vasoconstriction. The precise etiology of migraine is unknown. Reported evidence suggests that a genetically transmitted functional disturbance of intra- and extracranial circulation may be involved. Regional alterations in cerebral blood flow attributable to intracranial arterial vasodilation are known to accompany headache associated with migraine. Some investigators have attributed head pain associated with a migraine to substances released as a result of or associated with dilation of scalp arteries during an acute migraine episode (e.g. Berkow et al., ed., 1992, The Merck Manual of Diagnosis and Therapy, Merck Research Laboratories, Rahway, N.J., pp. 1425–1426).

Prodromal symptoms of an acute migraine episode include, but are not limited to, depression, irritability, restlessness, anorexia, scintillating scotomas, visual changes such as perception of stars or zig-zag lines, paresthesias, and hemiparesis. These prodromal symptoms may disappear shortly before the migraine is manifested, or may persist until or after the onset of the migraine.

The head pain associated with migraine may be unilateral or generalized. Nausea, vomiting, and photophobia often accompany migraines. Symptoms generally follow a pattern in an individual patient, except that unilateral head pain may not always be on the same side. Patients afflicted with migraine may experience migraines with a frequency between daily and only once in several months. An untreated acute migraine episode may endure for a long period, such as hours or days.

Approximately 17% of adult women and approximately 6% of adult men experience migraines each year (Stewart et al., 1994, Neurol. (Suppl. 4):S17–S23; Lipton et al., 1993 Neurology 43(Suppl. 3):S6–S10; Osterhaus et al., 1992, PharmacoEconomics 2:67–76). Migraines may occur at any age, but usually begin between ages 10 and 30. Migraines often partially or completely remit after age 50. Frequently, a history of migraines may be ascertained in the genealogy of a patient afflicted with migraine.

Various nonspecific medical and surgical procedures have been recommended to decrease the frequency of recurrence of migraines. Such procedures include surgery, counseling, participation of the patient in biofeedback procedures, and administration of methysergide, propanolol, a calcium channel blocker such as verapamil, an ergotamine preparation such as dihydroergotamine, or a serotonin receptor agonist such as sumatriptan. Some procedures to decrease the frequency of recurrence of migraines may offer benefit to certain patients, but are not useful for alleviating the pain associated with an acute migraine episode once it has begun.

Treatments which have been recommended for the treatment of an acute migraine episode include administration of aspirin, codeine, a serotonin agonist such as sumatriptan, ergot, ergotamine, caffeine, a narcotic, butorphanol tartrate, meperidine, or a combination of these compounds. Administration of any combination of these compounds has not offered satisfactory or sustained relief from the pain or other symptoms associated with an acute migraine episode in many patients. Furthermore, numerous side effects have been reported to accompany administration of these compounds, including dizziness, nausea, somnolence, fatigue, chest pain, cardiac infarction, hypertension, hypertensive crisis, chest-, face-, and neck-hyperemia, gastrointestinal upset, sedation, drug dependence, and the like. In addition, certain of these compounds are contraindicated for numerous patients such as pregnant women, nursing women, patients using monoamine oxidase inhibitors, patients having a history of ischemic heart disease, ulcer, gastritis, kidney disease, liver disease, and other diseases.

Currently popular migraine treatments involve administration of a pharmaceutically active agent which interacts with a serotonin receptor on cerebral arterial surfaces (Goadsby, 1995, In: *Migraine: Pharmacology and Genetics*, Sandler et al., Eds., pp. 67–81; Cambridge et al., 1995, Brit. J. Pharmacol. 114:961–968; Ferrari et al., 1995, Euro. J. Neurol. 2:5–21). Serotonin receptor agonists include sumatriptan (Imitrex™, Glaxo Wellcome Inc., Research Triangle NC), zolmitriptan (Zomig™, Zeneca Pharmaceuticals, Wilmington, Del.), and rizatriptan (Maxalt™, Merck & Co., West Point, Pa.). Serotonin receptor agonists are believed to produce relief from an acute migraine episode by causing resumption of regulated cranial blood flow, thereby halting the acute migraine episode. (Hamel et al., 1993 Mol. Pharmacol. 44:242–246). However, administration of serotonin receptor agonists is inefficient via intravenous, oral, and intrarectal gavage routes. These routes of administration result in systemic agonist distribution, which increases the availability of the agonist to hepatic tissue and to other sites where the agonists are metabolized. Furthermore, systemic distribution of one of an agonist results in distribution of the agonist to sites where the agonist produces undesirable side effects (Saper, 1997, Headache 37(Suppl. 1):S1–S14). Therefore, it would be advantageous to administer an agent which does not require systemic delivery.

Intranasal administration of lidocaine for the relief of pain associated with migraines has been investigated in a non-controlled study by Kudrow et al. (1995, Headache, 35:79–82). In that study, many patients experienced no relief and were on migraine prophylactic medication. In a controlled study, Maizels and co-workers evaluated the effectiveness of intranasally-administered lidocaine, a shorter-acting local anesthetic, for treatment of acute migraine episodes (Maizels et al., 1996, J. Amer. Med. Assoc. 276:319–321). High concentrations of lidocaine administered intranasally decreased head pain within fifteen minutes in 55% of the patients so treated. However, significant pain and associated symptoms persisted in many of these patients following treatment. A significant number of patients required further treatment with other types of migraine medication to attain acceptable relief. Furthermore, the acute migraine episode frequently rebounded or relapsed early after treatment, usually within the first hour.

Cluster Headaches

A cluster headache comprises a headache which is characterized by recurrent episodes of unilateral excruciating pain, usually occurring on the same side of the head of a patient. These headaches are typically oculofrontal or oculotemporal, with occasional radiation to the upper jaw, and are described as being of a boring, non-throbbing nature. Associated with the head pain are one or more autonomic accompaniments, including conjunctival injection, nasal congestion, lacrimation, rhinorrhea, body temperature elevation, vasodilation on the same side as that on which the pain is experienced, and edema beneath the eye. A cluster headache is usually of short duration, persisting for between fifteen and ninety minutes, and tends to occur in clusters—typically a few times a day for a period of six to twelve weeks. Months or years may pass between the clusters of headaches. Because headaches which appear to be identical to spontaneous cluster headaches may be induced by subcutaneous injection of histamine diphosphate, cluster headaches are also known as histamine headaches. Headaches having sensory similarity to cluster headaches may also be induced by administration of nitroglycerin to a human patient, for example by sublingual administration of 0.4 milligrams of nitroglycerin.

Methods which have been investigated for treating cluster headaches include administration of methysergide, a vasoconstrictor, a corticosteroid, oxygen, indomethacin, and intranasal administration of cocaine, which is a toxic shorter-acting local anesthetic with pronounced central effects and a vasoconstrictor, or lidocaine, which is also a shorter-acting local anesthetic (Barre, 1982, Headache, 22:69–73; Kittrelle et al., 1985, Arch. Neurol. 42:496–498). These investigations highlight that shorter-acting local anesthetics were effective to abort pain associated with a single individual headache episode that is only one of several headache episodes comprising a cluster headache, sometimes referred to as a cluster period. Large amounts of drug and repeated dosings were required to achieve these results. However, no investigation was made by those investigators of the ability of these shorter-acting local anesthetics to provide relief from all, or even more than one, of the typically short-duration headaches associated with a single cluster headache period. Clinically, intranasal administration of lidocaine has proven to be disappointing and is not widely used, nor is it included in recognized cluster headache treatment protocols.

Tinnitus

More than 37 million Americans are afflicted with tinnitus. Tinnitus is a condition characterized by a ringing, buzzing, roaring, or clicking sound perceived by a patient, a person observing the patient, or both, which seems to originate from the ear of the patient. Objective tinnitus is characterized by noise originating from the ear of a patient which can be perceived by a person examining the patient, while noise associated with subjective tinnitus can be perceived only by the patient. There are currently no truly effective treatment options available for tinnitus, which has been associated with instances of suicide in patients afflicted therewith. Treatment methods which have been attempted include surgical decompression of the eighth nerve, use of specialized hearing aids which mask the tinnitus, and infusion of drugs directly into areas of the brain involved in auditory sensory processing. None of these treatment methods has proven routinely effective.

Intra- and Extracranial Vasospasm

Intra- and extracranial vasospasm, hereinafter referred to as "cerebrovascular spasm," results from contraction of smooth muscle tissue of a cerebral blood vessel. Cerebrovascular spasm interferes with cerebral blood supply and is associated with numerous symptoms, including muscle paralysis, visual changes, speech changes, and numerous ischemic symptoms of stroke. Vascular muscle tone is modulated by neural, humoral and local factors.

Disorders Manifested During or After and Associated with an Acute Ischemic Event Causes of acute ischemic events include occlusive (i.e. thrombotic or embolic) processes, as well as vasospastic and other physiological processes and disorders, following the onset of which the affected tissue is insufficiently supplied with oxygenated blood. Manifestations during or after such events include, for example, tissue damage or death, vasospasm, vasodilation, vasomotor instability, muscle weakness, dysphasia, dysphonia, cognitive impairment, autonomic imbalance, and the like. These disorders may be alleviated by increasing oxygenated blood supply to the ischemic tissue. Increased blood supply to ischemic cerebral tissue may be effected, for example, by inducing dilation of an occluded cerebral blood vessel. Further by way of example, such increased blood supply may be effected by dilation of cerebral blood vessels proximal to an occluded vessel by increasing the flow of oxygenated blood or by increasing the pressure gradient across the occlusion, thereby decreasing the amount of watershed ischemia, decreasing the amount of damaged cerebral tissue, and increasing the amount of cerebral tissue which may be salvaged. Furthermore, facilitating venous drainage, by venodilation, decreases venous back pressure and increases forward flow of oxygenated blood.

Prior art methods of treating such disorders exhibit serious limitations. Thrombolytic therapy, for instance, is known to be effective to decrease the severity of cerebral damage caused by certain occlusive strokes if the therapy is performed soon enough after the onset of the occlusion. However, cerebrovascular spasm frequently follows, and decreases the success of the procedure and adversely affects patient outcome. A method of reducing the severity of an acute cerebral ischemic event by increasing early blood flow to the ischemic area and decreasing vasospasm is needed.

Anatomy of the Nasal Cavity

The structures associated with the nasal cavity are described, for example, in Williams et al. (eds., 1980, *Gray's Anatomy,* 36th ed., W.B. Saunders Co., Philadelphia, 1062–1065), especially at figures 3.78, 3.79, 3.80, 7.239, and 7.240 and the accompanying text. FIG. 1 herein is a diagram depicting the approximate location of the SPG in relation to the nasal cavity of a human.

The SPG is, in some texts, designated the "pterygopalatine ganglion." The position, origin, branches, and distribution of the SPG may be understood by examining figures 7.177, 7.178, 7.179, and 7.181 and the accompanying text in Williams et al. (supra).

As the cited figures and text describe, the SPG is located below a region of epithelium in the posterior portion of the nasal cavity, inferior to and including the spheno-ethmoidal recess, and is therefore not readily accessible via the nostril.

Ropivacaine is a recently introduced amino amide local anesthetic that is commercially available as the S(levo)-enantiomer (Lee et al., 1989, Anesth. Analg. 69:736–738). Ropivacaine allows differential nerve block and exhibits intermediate distribution and clearance and a better systemic toxicity profile compared with other similar relatively long acting potent local anesthetics. In addition, ropivacaine also exhibits inherent vasoactive properties (deJong, 1995, Reg. Anesth. 20:474–481; Santos et al., 1990, Anesth. Analg. 70:262–266). Ropivacaine-HCl is commercially available as 0.25%, 0.5%, 0.75% and 1.0% (w/v) solution (Naropin™, Astra USA, Inc., Westborough, Mass.), and has been described, for example in international patent application publication number WO 85/00599.

Local anesthetics are known to block the generation and the conduction of nerve impulses, presumably by increasing the threshold for electrical excitation in the nerve, by slowing the propagation of nerve impulses, and by reducing the rate of rise of the action potential of the nerve. In general, the progression of anesthesia is related to the diameter, degree of myclination, and conduction frequency and velocity of affected nerve fibers. Generally, the order of loss of nerve function is as follows: (1) sympathetic and parasympathetic function, temperature and pain, and (2) touch, and, where applicable, (3) proprioception, and (4) skeletal muscle tone.

The rate of systemic absorption in a patient of a local anesthetic is dependent upon the total dose, the concentration, and the identity of the local anesthetic administered to the patient, the route of administration, the vascularity of the site of administration, and the presence or absence of vasoconstrictors such as epinephrine in the anesthetic composition. A dilute concentration of epinephrine (e.g. 1:200,000 or 5 micrograms per milliliter) usually reduces the rate of absorption and peak plasma concentration of the local anesthetic, sometimes prolonging the duration of the anesthetic effect.

The duration of the anesthetic effect at a given site of administration of a local anesthetic is dependent upon the total dose, the concentration, and the identity of the local anesthetic administered to the patient, the rate of systemic absorption, and often the presence or absence of a vasoconstricting or other agent in the anesthetic composition.

Systemic administration of a local anesthetic is not a practical method for delivery of the local anesthetic to provide lasting relief of headache pain in a human patient, due to known adverse reactions, occasionally including acute emergencies, associated therewith.

There remains a significant unmet need for effective methods of treating acute CNvDs such as persistent and recurrent headaches of neurovascular etiology, including migraines and cluster headaches. Particularly needed are compositions and methods which are effective for inhibiting an acute neurovascular headache episode.

Muscular Headaches

Muscular headaches are very common in the adult population. It is estimated that between about 3% and about 5% of patients who experience a muscular headache are afflicted with chronic muscular headaches, by which is meant that the muscular headache occurs more than fifteen days per month for a period of at least about six months. Analgesic addiction is a recognized problem in the treatment of patients afflicted with chronic muscular headaches.

Muscular headaches may be acute, as is the case for typical episodic tension headaches, which are related to contraction of muscles of the head and neck. Sustained contractions of skeletal muscles of the head, neck, face, and shoulders are associated with concurrent local chemical changes within skeletal muscle, and may give rise to pain. The pain may be localized or it may be referred, which means that the pain is perceived at a body location different than the location of muscle contraction. Muscle contraction headaches may also be chronic and associated with depression or with one or more other psychological problems. Muscle contraction headaches may also be associated with anatomic factors such as cervical arthritis, temporomandibular joint disorders, irritating lesions, pressure and mechanical stress, eye strain, or emotional stress or disorders.

Muscular headaches, including muscle contraction headaches and tension headaches, are recognized as the most common category of recurring head pain. In distinction from migraines, they are usually bilateral, often with occipital nuchal, temporal, or frontal predominance or with diffuse extension over the top of the cranium. The pain may be located in the back of the head and neck as well. Unlike migraine pain, the pain associated with a muscular headache is usually described as squeezing and vise-like in nature. Nausea, photophobia, and phonophobia are not generally associated with muscular headache episodes. The onset of a muscular headache episode is more gradual than the onset of a migraine or cluster headache episode, and muscular headache episodes are not generally associated with auras or prodromal symptoms. The onset of muscular headache episodes does not appear to be associated with physical activity by the patient. Once established, a muscular headache episode may persist, perhaps with minimal fluctuations in intensity, for weeks or months. Muscular headache is recognized as being present all day, day after day.

Although patients afflicted with migraine may be awaked from sleep, patients afflicted with a chronic muscular headache generally sleep undisturbed and perceive development or intensification of the headache soon after waking. About a third of patients afflicted with a muscular headache exhibit symptoms of depression. Migraine headaches may be complicated by tension headaches which persist and arouse fears of mass lesions, thereby leading to the performance of unnecessary diagnostic workups in many patients.

Muscular headaches are recognized as being a distinct class of headaches, distinguishable from headaches such as migraines or cluster headaches.

Muscular headaches are, in part, related to sustained contraction of the skeletal muscles of the scalp, face, neck, and shoulders. Sustained muscle contraction is related to local pathology, central influences, and multisystem modulation, and involves gamma efferent neuronal muscle spindle activation. Related monosynaptic conduction through the ventral horn augments both efferent neuronal discharge and muscle contraction. A cycle of pain, muscle spasm, local chemical changes, neural excitability, skeletal muscle blood vessel compression or spasm, and anxiety ensues. All types of persistent headaches lead to sustained cranial muscle contraction, but pain resulting from this type of sustained contraction is typified by an aching sensation, rather than by the characteristic squeezing pain associated with muscular headaches. Sometimes, surface electromyograph recordings of the craniocervical muscles show no evidence of persistent contraction. It is therefore widely suspected that muscular headaches are not caused solely by sustained cranial muscle contraction.

Generally, the pain associated with a muscular headache episode is mild to moderate in severity, although the pain becomes severe in many patients. Relaxation, massage, and common analgesic medications such as aspirin and acetaminophen are often effective to alleviate mild muscular headache pain. Codeine or other narcotic preparations, tranquilizers, and antidepressants are sometimes administered to patients experiencing more severe muscular headache pain. Unfortunately, many of these patients develop physical dependence on these agents and must be followed closely because of a significant incidence of addiction.

Nonetheless, the musculature of the head, neck, jaw, or upper back is tense and tender in many or most patients afflicted with a muscular headache, and one or more trigger points, or muscle knots, are often present. Cervical spine arthritis and temporomandibular joint disorders may contribute to the development of a muscular headache.

Treatments which have been recommended for the treatment of muscular headaches include reassurance and psychological support, massage of the head and neck, application of hot and cold packs, transcutaneous electrical neural stimulation, physical support (e.g., use of orthopedic pillows and the like), administration of aspirin compounds, acetaminophen compounds, non-steroidal anti-inflammatory drugs, tricyclic antidepressants, narcotic analgesics, oral muscle relaxants, with or without tranquilizers, muscle relaxants, and other analgesic compounds. These treatments are generally effective for alleviating mild- to moderate-intensity acute muscular headaches.

Some patients afflicted with either severe or chronic muscular headaches sometimes experience relief from their acute symptoms using these known treatments. However, many do not. Furthermore, over time, many patients who initially respond to one or more of these therapies become less responsive to these therapies, possibly because they develop a tolerance to known medications, or because the disease process progresses or increases. Additionally, symptoms may be influenced by psychological factors which may remain constant or worsen. The side effects which accompany administration of known medications are significant and may become more severe over time.

There remains a significant unmet need for effective compositions and methods of treating muscular headaches, including inhibiting muscle contraction headaches and tension headaches. The present invention provides compositions and methods which satisfy this need.

Systemic Delivery of a Pharmaceutically Active Agent

Numerous pharmaceutically active agents are useful when delivered systemically to a human patient. Systemic delivery of such agents can sometimes be effected by oral administration of a composition comprising the agent. However, many pharmaceutically active agents are degraded by, or otherwise react with acids, proteins, or other agents located in, the human gastrointestinal tract or the human liver or circulatory system, with the result that the agent loses its pharmaceutical usefulness. For this reason, many pharmaceutically active agents may not practically be administered by an oral route to achieve systemic delivery of the agent. In addition, gastrointestinal absorption of an orally administered medication may be impaired in a distressed patient, such as a patient experiencing a migraine or any severe headache.

Pharmaceutically active agents intended for systemic delivery to a human may be administered via an intravenous route using well known methods. However, such methods cause discomfort to the patient and often can be performed only in conjunction with frequent or continuous supervision by a medical professional.

Methods of topically administering compositions to a human tissue to achieve systemic delivery of a pharmaceutically active agent which is a component of the composition are known, including the use of transdermal or transmucosal pastes, creams, liquids, solids and semisolids impregnated with the composition, and the like. Systemic delivery of a pharmaceutically active agent effected by topical administration methods are limited by the ability of the agent to diffuse through the tissue to which the composition is applied to reach blood vessels where the agent is absorbed and taken up for systemic delivery.

A significant, unmet need remains for compositions and methods which can be used to systemically deliver or to enhance systemic delivery of a pharmaceutically active agent to a human and which overcome the limitations of known systemic delivery compositions and methods.

The present invention provides compositions and methods which satisfy the needs described herein.

SUMMARY OF THE INVENTION

Figure 1:
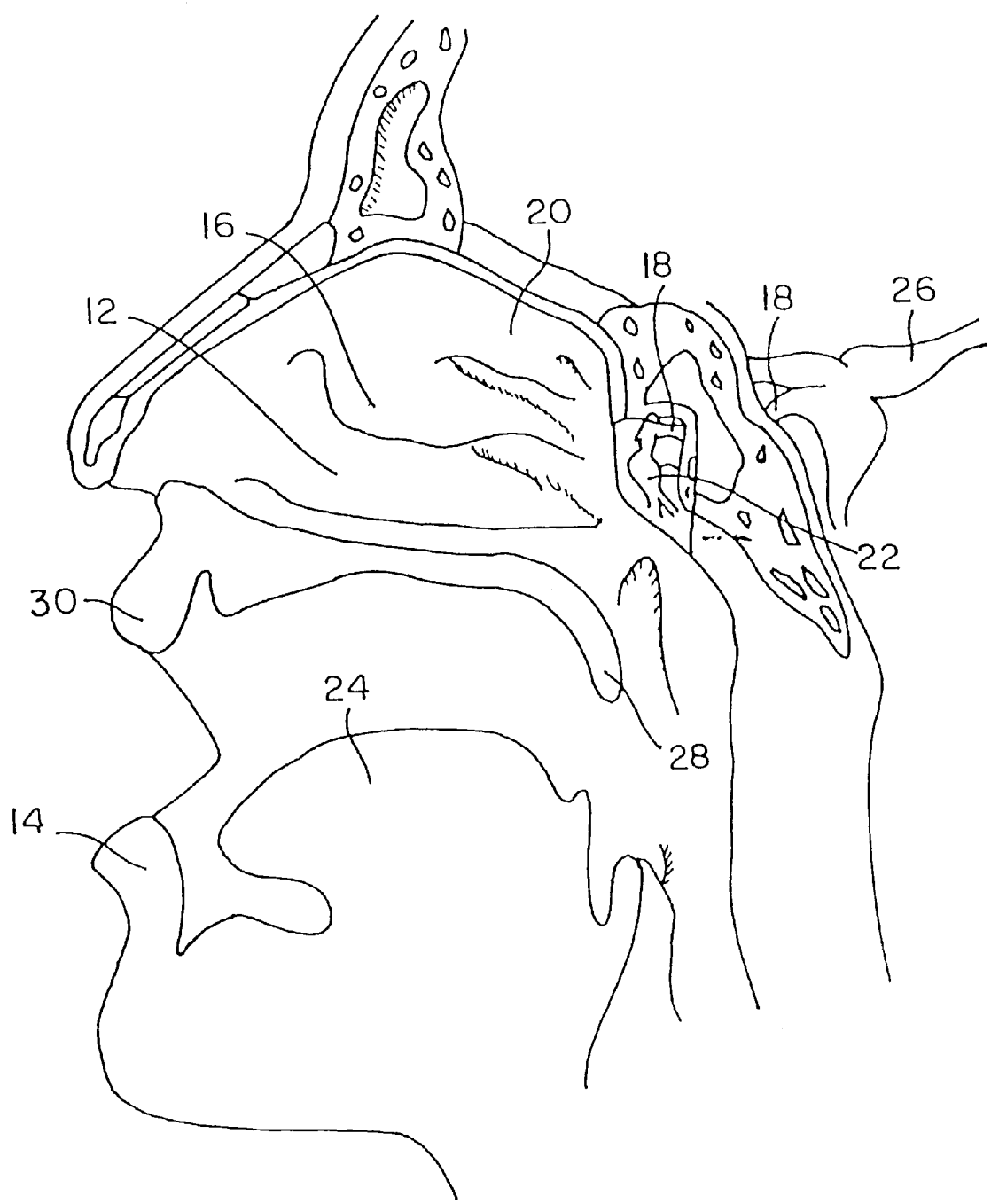
FIG. 1 is a diagram depicting a sagittal section of a portion of a human head, the section being just to the right of the nasal septum. A section is cut away at the posterior portion of the nasal cavity to reveal the approximate placement of the sphenopalatine ganglion. Indicia used in this Figure include 12 inferior concha, 14 lower lip, 16 middle concha, 18 maxillary nerve, 20 superior concha, 22 sphenopalatine ganglion, 24 tongue, 26 trigeminal nerve, 28 uvula, and 30 upper lip.
Figure 2:
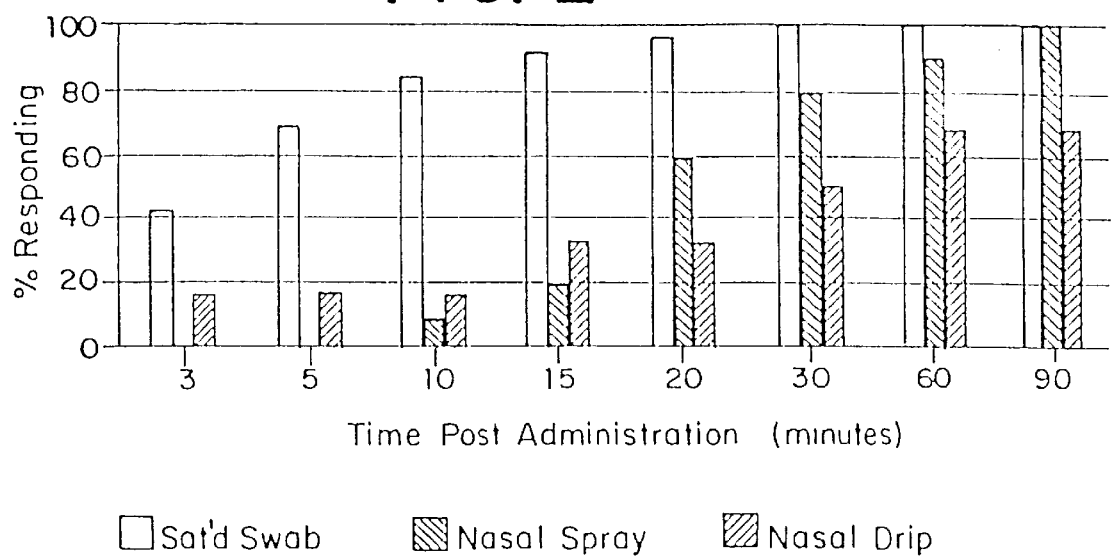
FIG. 2 is a bar graph which depicts the percentage of patients who exhibited at least 50% reduction in pain intensity following dorsonasal administration of ropivacaine using the intranasal spray method described herein ("Nasal spray"), using the intranasal drip method described herein ("Nasal drip"), or using the intranasal cotton swab method described herein ("Sat'd Swab").

One aspect of the invention relates to a method of inhibiting a cerebral neurovascular disorder (CNvD) in a human patient. This method comprises intranasally administering a long-acting local anesthetic pharmaceutical composition to the patient in an amount effective to inhibit the CNvD. The CNvD may, for example, be selected from the group consisting of tinnitus, cerebrovascular spasm, seizure, a disorder manifested during or after and associated with an acute ischemic event, and a neurovascular headache. Preferably, the CNvD is a migraine, such as an acute migraine episode.

According to this method, the long-acting local anesthetic pharmaceutical composition comprises a pharmaceutically acceptable carrier and at least one local anesthetic ingredient selected from the group consisting of a long-acting local anesthetic, a persistent local anesthetic, and a sustained release formulation of a local anesthetic.

In an alternate embodiment of this method, the long-acting local anesthetic pharmaceutical composition further comprises a pharmaceutically active agent such as one selected from the group consisting of a vasoconstrictor, epinephrine, norepinephrine, phenylephrine, methysergide, propanolol, a calcium channel blocker, verapamil, ergot, an ergotamine preparation, dihydroergotamine, a serotonin agonist, sumatriptan, zolmitriptan, rizatriptan, naratriptan, a chroman compound, aspirin, acetaminophen, a non-steroidal anti-inflammatory drug, caffeine, a narcotic, butorphanol tartrate, meperidine, a mast cell degranulation inhibitor, cromolyn sodium, eucalyptol, tetrodotoxin, desoxytetrodotoxin, saxitoxin, an organic acid, a sulfite salt, an acid salt, a glucocorticoid compound, a steroid ester, magnesium or lithium ions, a centrally-acting analgesic, a beta blocker, an agent that increases cerebral levels of γ-aminobutyric acid, butalbital, a drug that increases cerebral levels of γ-aminobutyric acid, a benzodiazepine, valproat, gabapentin, divalproex sodium, a tri-cyclic antidepressant, a narcotic analgesic, an oral muscle relaxant, a tranquilizer, and a muscle relaxant.

The invention also relates to a method of inhibiting a muscular headache in a human patient. This method comprises intranasally administering a local anesthetic to the patient in an amount effective to inhibit the muscular headache.

Another aspect of the invention relates to a method of inhibiting a cerebral neurovascular disorder in a human patient, comprising anesthetizing a nerve structure associated with the disorder in the patient for a period effective to inhibit the disorder. The effective period is at least about one hour, and is preferably at least about two hours.

The invention further relates to a pharmaceutical composition useful for inhibiting a cerebral neurovascular disorder or a muscular headache in a human patient. This composition comprises at least one local anesthetic and is formulated for intranasal delivery. A single intranasally administered dose of this composition inhibits the cerebral neurovascular disorder or muscular headache.

The invention also relates to a kit comprising the long-acting local anesthetic pharmaceutical composition of the invention and an applicator for intranasally administering the composition to the patient. The kit may also comprise instructional material which describes intranasal or dorsonasal administration of the composition to a human or another animal.

The invention still further relates to a method of systemically administering a pharmaceutically active agent to a mammal. This method comprises non-intravenously administering to the mammal a composition comprising a pharmaceutically effective amount of at least one local anesthetic and the pharmaceutically active agent.

DETAILED DESCRIPTION OF THE INVENTION

The first aspect of the present invention is based on the discovery that intranasal administration of a long-acting local anesthetic pharmaceutical composition to a human patient experiencing a cerebral neurovascular disorder (CNvD) inhibits the CNvD or a symptom of the CNvD. The invention also relates to the discovery that anesthesia of a dorsonasal nerve structure (DnNS) in a human patient experiencing a CNvD inhibits the CNvD or a symptom of the CNvD if the anesthesia persists for a period of at least about an hour, and preferably for a period of at least about two hours.

Local anesthetics are known to provide analgesia to a body surface to which they are applied. However, such analgesia persists only for a period of time which is characteristic of the particular local anesthetic used and the site anesthetized. Local anesthetics may be roughly divided into classes based on the duration of analgesia provided to a patient following topical administration.

It is known that intranasal administration of a relatively shorter-acting local anesthetics such as lidocaine or cocaine decreases head pain for a period approximately equal to the duration of analgesia which is characteristic of such shorter-acting local anesthetics. Lidocaine and cocaine each exhibit a duration of action shorter than about one hour when intranasally administered.

What was not known, and what represents a surprising discovery, is that intranasal, and preferably dorsonasal, administration of a local anesthetic preparation which either relieves a symptom of the CNvD for at least about one hour or exhibits a duration of anesthesia equal to at least about one hour is effective both to relieve head pain beyond the period of expected anesthesia and, more importantly, to inhibit the CNvD, such that symptoms of the CNvD, including head pain, do not rebound following the period of anesthesia, or even for many hours, days, or weeks thereafter. Rebound remains a major shortcoming of prior art treatments.

Definitions

As used herein, the term "cerebral neurovascular disorder" (CNvD) means a disorder which is characterized by one or more disturbances in the normal functioning of at least one component of the cerebral vascular or cerebral nervous system in a human. CNvDs which have been characterized include migraine, cluster headaches, other headaches of neurovascular etiology, tinnitus, and cerebrovascular spasm. An "acute" CNvD means an individual episode of a CNvD. Thus, an acute CNvD includes, but is not limited to, an acute neurovascular headache episode, a single episode of tinnitus, a single episode of cerebrovascular spasm, and a set of symptoms or a disorder manifested during or after and associated with an acute ischemic event such as a single cerebrovascular occlusion or a stroke.

As used herein, a CNvD or an acute CNvD or a muscular headache is "inhibited" if at least one symptom of an episode of the CNvD or the muscular headache is alleviated, terminated, or prevented. As used herein, a CNvD or muscular headache is also "inhibited" if the frequency of recurrence, the severity, or both, of acute CNvD or muscular headache is reduced.

As used herein, the term "muscular headache" means head, neck, face, periocular, scalp, or upper back pain associated with contraction of muscles of the head, neck, jaw, or upper back of a patient. The head pain may be experienced in or around a muscle, or it may be referred to a part of the head or upper back distinct from the site of the affected muscle. It is understood that the term "muscular headache" includes both acute and chronic episodes of head pain. By way of example, muscular headaches include muscle contraction headaches and tension headaches.

As used herein, a CNvD or a muscular headache is "terminated" if at least one symptom of the CNvD or muscular headache ceases in a patient and the patient does not experience the symptom for at least several hours or, preferably, for at least about one day.

As used herein, a "recurring" CNvD is a CNvD which is experienced by a patient more than once in a six-month period.

As used herein, the term "acute ischemic event" refers to a single episode experienced by a human patient wherein a tissue of the patient is insufficiently supplied with oxygen. Acute ischemic events include, for example, ischemia associated with a stroke, ischemia associated with vasospasm, and ischemia associated with an acute neurovascular headache episode.

As used herein, the term "neurovascular headache" means a headache of neurovascular etiology associated with a disease, disorder, or imbalance of the nervous or vascular systems in a human. Headaches of neurovascular etiology include, but are not limited to, migraines and cluster headaches.

As used herein, the term "acute neurovascular headache episode" means a single neurovascular muscular headache which either has a duration greater than about one hour or recurs more than once in a one-day period in a human patient. Examples of acute neurovascular headache episodes include, but are not limited to, a single persistent neurovascular headache, an acute migraine episode, each of the individual headache episodes associated with a recurrent neurovascular headache, and each of the individual headache episodes associated with a cluster headache.

As used herein, the term "acute muscular headache episode" means a single muscular headache. Examples of acute neurovascular headache episodes include, but are not limited to, a single muscle contraction headache and a single tension headache.

As used herein, the term "chronic muscular headache" means a muscular headache muscular which is experienced by a human patient more than fifteen days per month for a period of at least about six months.

As used herein, the term "persistent neurovascular headache" means a headache of neurovascular etiology which persists for a period longer than about one hour.

As used herein, the term "recurrent neurovascular headache" means a headache of neurovascular etiology which is experienced by a human patient more than once in a one-day period.

As used herein, the term "rebound" of a CNvD means experience by a patient of one or more symptoms of the CNvD following a period during which the patient did not experience the one or more symptoms, the symptom-free period having been preceded by an earlier period during which the patient experienced one or more symptoms of the CNvD. It is understood that it is not always possible to discern whether a patient who did not experience the one or more symptoms for a period is afflicted with the same episode or with a separate episode of the same CNvD. Thus, the term is inclusive of both situations.

As used herein, the term "migraine" means a human disorder characterized by at least one persistent neurovascular headache episode.

As used herein, the term "an acute migraine episode" means an individual headache experienced by a human patient afflicted with migraine.

As used herein, the term "cluster headache" means a human disorder characterized by recurrent neurovascular headaches of short duration.

As used herein, the term "individual headache episode associated with a cluster headache" means a single neurovascular headache experienced by a human patient afflicted with cluster headache.

As used herein, the term "prodromal headache symptom" means a symptom which is experienced by a patient and which is associated with the onset or indicates the imminent onset of an acute neurovascular headache episode.

As used herein, a "nerve structure" means a nerve, a plurality of nerves located in close anatomic proximity to one another, or a ganglion.

As used herein, a nerve structure is "associated with" a CNvD if, when the nerve structure is anesthetized in a human patient afflicted with the disorder, the patient experiences relief from at least one symptom of the CNvD.

As used herein, a "dorsonasal nerve structure" (DnNS) means the sphenopalatine ganglion (SPG) or a nerve structure located in close anatomic proximity to the SPG.

As used herein, a first nerve structure is located in "close anatomic proximity" to a second nerve structure if the second nerve structure is anesthetized following anesthesia of the first nerve structure effected by administration of a local anesthetic to a tissue which comprises or overlies the first nerve structure. It is believed that dorsonasal administration of a local anesthetic anesthetizes at least one, and perhaps all, of the SPG, the cavernous sinus ganglion, the carotid sinus ganglion, numerous branches of the maxillary nerve, the ethmoidal nerve, the ethmoidal ganglion, and the vidian nerve. Thus, by way of example, each of the cavernous sinus ganglion, the carotid sinus ganglion, numerous branches of the maxillary nerve, the ethmoidal nerve, the ethmoidal ganglion, and the vidian nerve is located in close anatomic proximity to the SPG, and thus each is a DnNS.

As used herein, a nerve structure is "anesthetized" when the capacity of the ganglion to generate or conduct nerve impulses is significantly impaired, relative to the capacity of the nerve structure to generate or conduct nerve impulses in the absence of intervention, such as by administration of a local anesthetic. Anesthesia of the SPG effected by administration of a local anesthetic, for example, interrupts the functioning normally associated with the SPG and with other DnNSs. It is understood that anesthesia of a nerve structure may be achieved not only using a local anesthetic, but also by any anesthetic method as set forth herein.

As used herein, the capacity of a DnNS to generate or conduct nerve impulses is "significantly impaired" when that capacity is reduced by an amount sufficient to relieve the pain associated with a headache of neurovascular origin in a patient afflicted with such a headache.

As used herein, the term "shorter-acting local anesthetic" means a local anesthetic which, when intranasally administered to a human patient experiencing a CNvD or a muscular headache, relieves at least one symptom of the CNvD or muscular headache for a period of less than about one hour. By way of example, lidocaine and cocaine are shorter-acting local anesthetics.

As used herein, the term "long-acting local anesthetic" means a local anesthetic which, when intranasally administered to a human patient experiencing a CNvD or a muscular headache, reliably or consistently relieves at least one symptom of the CNvD or muscular headache for a period of at least about one hour. By way of non-limiting examples, bupivacaine and ropivacaine are long-acting local anesthetics.

As used herein, the term "persistent local anesthetic" means a local anesthetic which, when intranasally administered to a human patient experiencing a CNvD or a muscular headache, relieves at least one symptom of the CNvD or muscular headache for a period of at least about two hours.

As used herein, the terms "vasoconstrictor" and "vasoconstricting agent" are used interchangeably to mean an agent which induces diminution of the luminal caliber of a blood vessel. The agent may be a chemical compound or a stimulus applied to a motor neuron which causes vasoconstriction. Hence, administration of a vasoconstrictor may comprise administration of a chemical compound, application of such a stimulus, or both. Vasoconstrictors include, but are not limited to, epinephrine, norepinephrine, and phenylephrine.

As used herein, the terms "vasodilator" and "vasodilating agent" are used interchangeably to mean an agent which induces an increase in the luminal caliber of a blood vessel.

As used herein, the term "intranasal administration" of a composition and grammatical forms thereof mean delivery of the composition to any portion of the nasal epithelium.

As used herein, the term "dorsonasal administration" of a composition and grammatical forms thereof mean delivery of the composition to a tissue, fluid, or surface of a human, whereby a component of the composition is provided to a DnNS or to a tissue overlying a DnNS. Dorsonasal administration may be accomplished, for example, by topical administration of the composition to the region of the nasal epithelium overlying the SPG or to the surface of the nasal epithelium near the region of the nasal epithelium overlying the SPG, whereby a component of the composition is capable of diffusing through any tissue or fluid which may be interposed between the surface and the SPG. Such administration may also be accomplished, for example, by injecting the composition directly into the SPG or by injecting the composition into or otherwise administering the composition to a tissue or fluid near the SPG, whereby a component of the composition is capable of diffusing through any tissue or fluid which may be interposed between the site of injection or administration and the SPG.

As used herein, the term "the region of the nasal epithelium overlying the SPG" means the area of the nasal epithelium having a geometrical relationship with the SPG whereby an imaginary line approximately perpendicular to the surface of the epithelium and extending from the surface of the epithelium in the direction of the basement membrane of the epithelium passes through a DnNS.

As used herein, the term "the surface of the nasal epithelium near the region of the nasal epithelium overlying the SPG" means a portion of the surface of the nasal epithelium which is continuous with and sufficiently geometrically close to the region of the nasal epithelium overlying the SPG such that a compound applied anywhere on this surface is able to diffuse to the SPG. It is understood that the boundaries of the surface are dependent upon the diffusivity of the compound in the epithelium and in any tissue or fluid situated between the epithelium and the SPG. Thus, the area of this surface will be greater for a compound having high diffusivity than the area corresponding to a compound having a lower diffusivity. It is further understood that, where the compound has a half-life in vivo, the boundaries of "the surface of the nasal epithelium near the region of the epithelium overlying the SPG" are dependent upon the half-life of the compound. Thus, the area of this surface will be greater for a compound having a longer half-life than the area corresponding to a compound having a shorter half-life.

In the case of a compound having a diffusivity and a half-life comparable to that of ropivacaine, "the surface of the nasal epithelium near the region of the epithelium overlying the SPG" includes, but is not limited to, the surface of the region of the nasal epithelium overlying the SPG and the surface of the nasal epithelium continuous with and located within about three centimeters of that region. Preferably, such a compound is delivered to the surface of the nasal epithelium within about two centimeters of that region, and even more preferably to the surface of the nasal epithelium within about one centimeter of that region. Most preferably, the compound is delivered to the surface of the nasal epithelium overlying the SPG. It is understood that, in the case of a local anesthetic such as ropivacaine, the surface includes the epithelial surface covering the dorsal surface of the nasal cavity extending caudally from approximately the superior extent of the sphenoethmoidal recess to approximately the inferior boundary of the nasopharynx and extending laterally between the region of the surface covering the perpendicular plate of the right palatine bone and the region of the surface covering the perpendicular plate of the ethmoid bone and between the region of the surface covering the perpendicular plate of the left palatine bone and the region of the surface covering the perpendicular plate of the ethmoid bone.

As used herein, the term "non-intravenous administration" of a composition means administration of the composition by any means other than injection or infusion of the composition directly into the bloodstream of a human patient.

As used herein, the term "long-acting local anesthetic pharmaceutical composition" means a chemical composition comprising a pharmaceutically acceptable carrier and at least one local anesthetic ingredient selected from the group consisting of a long-acting local anesthetic, a persistent local anesthetic, and a sustained release formulation of a local anesthetic, wherein administration of the composition to a patient experiencing a CNvD or muscular headache inhibits the CNvD or muscular headache.

As used herein, the term "pharmaceutically acceptable carrier" means a chemical composition with which a local anesthetic may be combined and which, following the combination, can be used to administer the local anesthetic to a human patient without significantly adversely affecting the patient.

As used herein, "a sustained release formulation of a local anesthetic" is a pharmaceutical composition comprising a local anesthetic, wherein upon administration of the composition to a tissue of a human patient, the local anesthetic is delivered to the tissue on a continuous or semi-continuous basis for a period of hours, days, or weeks. Methods of making and using sustained release formulations of local anesthetics are well within the skill of one of ordinary skill in the art of pharmacology. In addition, inclusion of a vasoconstrictor in the composition may prolong the duration of the anesthetic effect.

As used herein, a composition is "formulated for intranasal delivery" if the composition is susceptible of intranasal administration to a human and if the composition is not significantly injurious to the tissues lining the nasal cavity of a human.

As used herein, the term "pharmaceutically active agent" means a composition which, when administered to a human patient, has a biochemical or physiological effect on the patient.

As used herein, "instructional material" includes a publication, a sound, video, or other recording, a diagram, or any other medium of expression which can be used to communicate the usefulness of the composition of the invention for inhibiting a CNvD or a muscular headache. The instructional material of the kit of the invention may, for example, be separate from, included with, or affixed to a container which contains the composition of the invention or be shipped together with a container which contains the composition. The instructional material may, for example, describe an appropriate dose of the composition of the invention or directions for using an applicator included in the kit to intranasally or dorsonasally administer a local anesthetic.

As used herein, a "eutectic mixture" is a mixture comprising at least one local anesthetic and at least one eutectic ingredient.

As used herein, a "eutectic ingredient" is a chemical compound which, when mixed with a local anesthetic, yields a mixture having a melting point lower than the melting point of the local anesthetic.

DESCRIPTION OF THE INVENTION

Inhibition of a Cerebral Neurovascular Disorder

One aspect of the invention is based on the discovery that intranasal, and preferably dorsonasal administration of a long-acting local anesthetic pharmaceutical composition to a human patient experiencing a cerebral neurovascular disorder (CNvD) inhibits the CNvD. The long-acting local anesthetic pharmaceutical composition comprises a local anesthetic ingredient selected from the group consisting of a long-acting local anesthetic, a persistent local anesthetic, and a sustained release formulation of a local anesthetic. The duration of relief from a symptom of a CNvD effected by intranasal administration of the long-acting local anesthetic pharmaceutical composition according to this method is at least about one hour, and is preferably at least about two hours. However, the duration may be at least about seventy-five, ninety, one hundred and five, or any other number of minutes such that the effective duration of relief is greater than that effected by intranasal administration of either lidocaine sometimes referred to herein as 2-(diethylamino)-N-(2,6dimethylphenyl)acetamide, its Chemical Abstracts name, or cocaine.

Intranasal, and preferably dorsonasal, administration of at least one long-acting or persistent local anesthetic, such as bupivacaine or ropivacaine, to a human patient experiencing a CNvD is sufficient to inhibit the CNvD or a symptom of the CNvD. Furthermore, intranasal or dorsonasal administration of a composition comprising a sustained release formulation of a shorter-acting local anesthetic inhibits the CNvD or a symptom thereof. By way of example, the CNvD may be a neurovascular headache, tinnitus which does not accompany a neurovascular headache, a cerebrovascular spasm which does not accompany a neurovascular headache, or an acute CNvD.

Symptoms of an acute neurovascular headache episode which can be inhibited by intranasal or dorsonasal administration of a long-acting local anesthetic pharmaceutical composition include, but are not limited to, head pain, tinnitus, visual changes, phonophobia, photophobia, nausea, seizure, cerebrovascular spasm, symptoms of acute ischemic events, such as muscle weakness, dysphasia, dysphonia, cognitive impairment, autonomic imbalances, and the like.

Prior art methods of treating an acute CNvD often transiently and/or incompletely relieve head pain, the primary symptom of many CNvDs. In contrast, the compositions, kits, and methods of the present invention provide lasting and effective relief of the symptoms of a CNvD. Without wishing to be bound by any particular theory, it is believed that intranasal administration of a long-acting local anesthetic pharmaceutical composition to a patient experiencing a CNvD provides relief by inhibiting the physiological processes underlying the CNvD, whereby both the CNvD and symptoms of the acute CNvD are inhibited.

Prevention of an Acute Cerebral Neurovascular Disorder

The method described herein for inhibiting an acute CNvD includes a method of preventing a CNvD. Certain CNvDs, particularly migraines, are associated with prodromal symptoms which are experienced by a patient prior to the onset of the disorder. By treating a patient using the method described herein for inhibiting a CNvD at a time when the CNvD is expected or at a time when a prodromal symptom of the CNvD is experienced by the patient, the CNvD may be prevented.

Decreasing the Frequency and/or Severity of Recurring CNvDs

Numerous cerebral CNvDs including, but not limited to migraines and TIAs, are characterized by periodic or irregular recurrence. Over time, severity of CNvDs often seems to increase and many CNvD-afflicted patients seem to experience CNvD episodes more frequently. It was observed that the frequency of recurrence and severity of CNvD episodes decreased with time in patients using the compositions and methods described in the present disclosure, even after treatment was no longer administered. These phenomena have not been previously observed with any other CNvD treatment method, including any migraine treatment method. The compositions, kits, and methods of the invention are useful for decreasing the frequency of recurrence, the severity, or both, of CNvD episodes experienced by a patient afflicted with recurring CNvDs such as migraines and TIAs.

The invention thus includes a method of decreasing the frequency or severity with which CNvD episodes are experienced by a patient afflicted with a recurring CNvD. The method comprises intranasally, and preferably dorsonasally, administering to a patient experiencing a CNvD episode a long-acting local anesthetic pharmaceutical composition. The composition comprises a local anesthetic which is preferably a long-acting local anesthetic, a persistent local anesthetic, or a sustained release formulation of a shorter-acting or a long acting or a persistent local anesthetic, and is preferably administered to the patient early in the course of the CNvD episode. Preferably, the local anesthetic is administered to the patient within two hours following the onset of the episode, more preferably within one hour, and even more preferably within thirty minutes of the onset. Early administration provides more prompt relief, but administration of the local anesthetic according to this invention may be at any time with good results.

Other Acute Cerebral Neurovascular Disorders

Intranasal, and preferably dorsonasal, administration of a local anesthetic can also be used to treat any CNvD, in addition to migraines or other neurovascular headaches. Examples of acute CNvDs other than acute neurovascular headache episodes include, but are not limited to, tinnitus, seizures or seizure-like activities, cerebrovascular spasm, and disorders manifested after and associated with an acute ischemic event such as a stroke, reversible ischemic neurological deficit, or transient ischemic attack. The local anesthetic compounds, formulations, dosages, and methods of administration which are useful for inhibiting these CNvDs are substantially the same as those described herein with respect to inhibiting a neurovascular headache. Where the acute CNvD is associated with cerebral ischemia, the amount of brain tissue which experiences ischemic damage may be reduced by this method.

Tinnitus and these other CNvDs may also be inhibited by anesthetizing a DnNS using alternate anesthetic methods including, but not limited to, transcutaneous electrical neural stimulation, electromagnetic techniques, application of radio frequency radiation, and surgical intervention to sever or disrupt the DnNS.

Duration of Anesthetic Effect

It has been discovered that intranasal administration of a long-acting local anesthetic pharmaceutical composition is necessary in order to inhibit a CNvD in a human patient. That is, intranasal administration of relatively shorter-acting local anesthetic compositions, such as a lidocaine-containing composition which is not a sustained release formulation, provides only transient relief (i.e. less than about one hour) from CNvD symptoms, without inhibiting the CNvD.

It is preferable that the long-acting local anesthetic pharmaceutical composition of the invention, when administered intranasally, and preferably dorsonasally to a patient experiencing a CNvD, inhibits at least one symptom of the CNvD for a period of at least about one hour. Thus, as described herein, compositions comprising bupivacaine or ropivacaine are effective for inhibiting a CNvD when administered intranasally to a patient, while compositions comprising lidocaine in a non-sustained release formulation are not effective for inhibiting a CNvD. Thus, the long-acting local anesthetic pharmaceutical composition preferably comprises a local anesthetic ingredient which relieves at least one symptom of a CNvD for a period greater than the period of relief provided by intranasal administration of lidocaine, and more preferably relieves the symptom for at least about as long as ropivacaine.

It is believed that anesthesia of a DnNS for a period of at least about one hour, or preferably at least about two hours, results in inhibition of both the symptoms and the physiological processes of a CNvD, including sterile inflammation and vascular lability, associated with neurovascular headache episodes such as migraines and cluster headaches. Thus, for example, a migraine and its accompanying symptoms may be inhibited by intranasally, and preferably dorsonasally, administering a long-acting local anesthetic, a persistent local anesthetic, or a sustained release formulation of a local anesthetic to a patient experiencing the migraine and its symptoms. Preferably, the period is one which is effective to terminate these processes, whereby both the processes and the symptoms associated with the CNvD are terminated.

At least one investigator (Barre, 1982, Headache 22:69–73) has investigated the use of cocaine, a toxic, addictive, shorter-acting local anesthetic with well-known potent central nervous system properties, to relieve the pain associated with an individual headache episode associated with a cluster headache.

The addictive, toxic, and central nervous system excitatory qualities of cocaine render it an inappropriate treatment in virtually all current clinical settings. Hence, it is preferable that the local anesthetic used in the method of the invention be a local anesthetic other than cocaine. Thus, it is preferred to use a long-acting local anesthetic, a persistent local anesthetic, or a sustained release form of a shorter-acting local anesthetic other than cocaine in the methods of the invention.

Prior art investigations have examined the effectiveness of lidocaine, a shorter-acting local anesthetic, for providing relief from headaches of neurovascular origin (Kittrelle et al., 1985, Arch. Neurol. 42:496–498; Kudrow et al., 1995, Headache, 35:79–82; Maizels et al., 1996, J. Amer. Med. Assoc. 276:319–321). These investigations involved intranasal administration of 4% (w/v) lidocaine, wherein the doses were sometimes repeated. Although many patients in these studies experienced a short term decrease in head pain, a significant number of these patients required supplemental medication with other known headache therapeutic agents and the rate of rebound was high.

Not recognized by these investigators was the fact that their investigations were hampered by the incapacity of lidocaine to provide consistent, long-lasting relief from the CNvD for a period of at least about one hour. Hence, although intranasal administration of high concentrations of lidocaine provided short term pain reduction, the acute neurovascular headaches experienced by the patients worsened or rebounded when the anesthetic effects of lidocaine subsided, within about an hour. Any effect which long-acting local anesthetics might have had upon inhibiting acute neurovascular headache episodes in the patients involved in those investigations was not recognized. The fact that no further development of lidocaine or its derivatives as the primary pharmaceutically active agent for persistent or recurring neurovascular headache relief was pursued, despite the critical need for such agents, is further evidence that the importance of the period of inhibition of at least one symptom of the CNvD, such as a period on the order of at least about one hour, and preferably at least about two hours, was not recognized as being useful to abort the physiologic pathology of sterile inflammation and vasomotor instability which, when not aborted, triggers another headache episode upon subsidence of the anesthetic effect of the shorter-acting local anesthetic.

The results of studies by Kudrow et al. (1995, Headache, 35:79–82), Maizels et a l. (1996, J. Amer. Med. Assoc. 276:319–321), and Barre (1982, Headache 22:69–73) can be explained by the model of CNvDs presented herein, wherein a DnNS such as the SPG is involved in the pathogenesis of headaches of neurovascular etiology. None of these prior art studies recognized that the severely limited effectiveness of intranasal administration of either lidocaine or cocaine for the alleviation of pain associated with a headache of neurovascular etiology was due to the fact that lidocaine and cocaine are merely shorter-acting local anesthetics when used in this manner. Indeed, repeat doses of cocaine and lidocaine were needed to treat individual and subsequent short duration headache episodes associated with a cluster headache.

Inhibition of a CNvD such as an neurovascular headache requires intranasal, and preferably dorsonasal, administration of a long-acting local anesthetic pharmaceutical composition which provides relief from a symptom of the CNvD for a period longer than that effected by the treatments in the investigations of Kudrow et al., Maizels et al., and Barre, namely for a period of at least about one hour, and preferably at least about two hours.

Shorter-acting local anesthetics are not consistently or reliably effective for inhibiting a CNvD when administered in a single dose or in multiple doses administered over a short period of time such as a few minutes. Nonetheless, using the teachings of the present invention, it is possible to use shorter-acting local anesthetics in a manner more effective to inhibit a CNvD without causing the side effects associated with repetitive dosing of these agents at high concentration. In order to inhibit a CNvD, it is necessary that a shorter-acting local anesthetic be intranasally, and preferably dorsonasally, administered as a sustained release formulation, or that an additional compound which extends the duration of anesthesia effected by the shorter-acting local anesthetic, such as epinephrine or another vasoconstrictor, be co-administered to the patient. Preferably the additional compound is administered to the patient in a composition comprising the local anesthetic and the additional compound. Compounds, formulations, and dosages of the vasoconstrictors described in this method are known in the art. For example, vasoconstrictive compositions may be used at art-recognized effective doses, such as, about 0.001 milligram per milliliter to about 0.01 milligram per milliliter of epinephrine. Similarly, the other additional compounds described in this paragraph may be used at art-recognized effective doses.

Theory Proposed to Explain the Efficacy of the Compositions and Methods of the Invention for Inhibiting a Neurovascular Headache It should be appreciated that the superiority of the compositions and methods of the invention relative to the compositions and methods of the prior art does not depend upon the accuracy of the theory offered to explain the superior results.

While not wishing to be bound by any particular theory of operation, it is believed that intranasal administration of the composition of the present invention inhibits a neurovascular headache by anesthetizing a dorsonasal nerve structure (DnNS) in the patient for a period effective to inhibit the physiological processes that result in the neurovascular headache, such as a period on the order of at least about an hour, and preferably at least about two hours.

Still without wishing to be bound by any particular theory, it is believed that the following model explains the physiological processes underlying an acute neurovascular headache. An acute neurovascular headache generation center (ANvHGC) is located in the pons of the human brain, near the locus coeruleus. The ANvHGC initiates an excitatory signal which affects the reticular formation, the trigeminal nerve, and sympathetic, parasympathetic, and other outflows from the midbrain and pons. Trigeminal nerve fibers innervate cerebral blood vessels and modulate vasomotor function and intra- and extracranial blood vessel tone and communicate with multiple neural structures. Stimulation of the trigeminal nerve by the ANvHGC results in changes in efferent and afferent neural activity and changes in regional intracranial blood flow. Many factors, including stimulation of the trigeminal nerve by the ANvHGC, facilitate neurogenic inflammation and associated vasomotor and other changes, including, but not limited to, monocytic and lymphocytic infiltrates, perivascular edema, and release of neurohumoral and other chemical factors. This results in intra- and extracranial neural and vascular hyperexcitability. This hyperexcitability decreases the threshold for neuronal and humoral signaling and other triggers which induce further vasospasm or further neuronal hyperexcitability and altered efferent and afferent activity. Prolonged vasospasm leads to tissue ischemia, which induces further release of neurohumoral factors, increases perivascular edema, and exacerbates neurogenic inflammation. These local neurovascular changes induce greater neuronal and vascular hyperexcitability. All of these factors contribute to the pathophysiologic cycle of neurovascular headache.

Altered cerebral blood flow, neurogenic inflammation, and associated vasomotor and other changes are experienced by the patient as head pain, tinnitus, symptoms of cerebrovascular spasm such as visual changes, blindness, or disorientation, or some combination of these, and contribute to the prodromal and other symptoms of an acute neurovascular headache.

Even in the absence of head pain, intracranial and extracranial blood vessel hyperexcitability and neuronal hyperexcitability can lead to recurrence or rebound of an acute neurovascular headache, such as a migraine, or to prolongation of the physiology of the neurovascular headache cycle. Thus, an alternate neurovascular headache cycle may include a period during which symptoms of the neurovascular headache are not perceived by the patient, but during which period intracranial and extracranial blood vessels and nerves remain hyperexcitable, as in the case of a series of individual headache episodes associated with a cluster headache or a recurrent migraine.

Further, without wishing to be bound by any particular theory, it is believed that intranasal administration of a shorter-acting local anesthetic such as lidocaine or cocaine merely provides analgesia alone by inhibiting transmission of nerve impulses for a relatively short period—less than about an hour. Administration of a shorter-acting local anesthetic does not interrupt the physiological processes which cause the pain associated with an acute CNvD such as an acute neurovascular headache episode. The duration of the anesthetic effect of a shorter-acting local anesthetic such as lidocaine is too short to permit intracranial and extracranial blood vessels and nerves to recover from the hyperexcitable state. The duration of the anesthetic effect of a shorter-acting local anesthetic is also too short to allow clearance of vascular and perivascular humoral and cellular factors from cerebrovascular tissue. The result of the short duration of the anesthetic effect of a shorter-acting local anesthetic is that the neurogenic inflammation continues, the neurovascular headache cycle persists, and, once the anesthetic effect of the shorter-acting local anesthetic subsides, the neurovascular headache rebounds.

In contrast, in accordance with the present invention, anesthesia of a DnNS such as the SPG for an effective period that permits intracranial and extracranial nerves and intracranial and extracranial blood vessels to recover from the hyperexcitable state, arrests neurogenic inflammation, and permits clearance of vascular and perivascular humoral and cellular factors from cerebrovascular tissue, inhibits the physiological processes which cause the occurrence or persistence of an acute neurovascular headache. The effective period of such anesthesia must be sufficient to affect these physiological processes in a beneficial manner, such as a period on the order of at least about an hour, and preferably at least about two hours. It is understood that the effective period may vary among individuals.

Compromised cerebral vascular flow volume and neurogenic inflammation are believed to be related to neural and humoral factors including increased local concentrations of nitric oxide, vasoactive intestinal peptide (VIP), substance P, and other factors present in ischemic or inflamed tissue. It is believed that the mechanism by which neurogenic inflammation is arrested and recovery of nerves and blood vessels from their hyperexcitable state is permitted following anesthesia of a DnNS, such as the SPG, for an effective period of time involves neuronal stabilization and clearance from intra- and extracranial neuronal and vascular tissues of nitric oxide, VIP, substance P, one or more neurotransmitters, one or more peptides, cellular infiltrates, or a combination of these factors. Concomitantly, blood vessel permeability is normalized and perivascular edema decreases. Anesthesia of the DnNS for the effective period furthermore limits release of humoral agents in cerebrovascular tissue and decreases vasoconstriction and, by inhibition of neural mediated increases in blood vessel smooth muscle tone, may effect vasodilation, thereby permitting dissipation of local humoral and cellular factors associated with head pain and other symptoms. The result is that when the anesthetic effect of the local anesthetic subsides, the cranial nerves and vascular structures are no longer hyperexcitable, neurogenic inflammation has been arrested or reversed, local humoral and cellular factors have dissipated, and thus the neurovascular headache cycle does not continue or rebound. This model represents a possible explanation of the superiority of the compositions and methods of the invention for inhibiting an acute neurovascular headache, relative to the compositions and methods of the prior art, which were ineffective or of very limited effectiveness for inhibiting such disorders.

The ability to block nerve fibers which mediate the processes involved in the headache cycle varies with the particular local anesthetic used. Shorter-acting local anesthetics do not exhibit the same degree of differential blockade (i.e. sensory blockade compared with autonomic blockade) exhibited by long-acting and persistent local anesthetics. Without wishing to be bound by any particular theory, it is believed that the anti-neurovascular headache efficacy exhibited by long-acting and persistent local anesthetics, relative to the non-efficacy of shorter-acting local anesthetics, may be attributable in whole or in part to the degree of differential blockade capabilities exhibited by these types of local anesthetics.

One aspect of the present invention may be explained, at least in part, by the hypothesis that intranasal, and preferably dorsonasal, administration of a long-acting local anesthetic pharmaceutical composition inhibits an acute CNvD such as an acute neurovascular headache episode. This treatment is hypothesized to result in anesthesia of a DnNS such as the SPG for a period of at least about one hour, and preferably for a period of about two hours.

Anesthesia of a DnNS such as the SPG may be achieved in any of a number of ways. For example, at least one long-acting or persistent local anesthetic may be intranasally or dorsonasally administered to a patient to effect anesthesia of the DnNS. Further by way of example, a sustained release formulation of a shorter-acting, long-acting, or persistent local anesthetic may be dorsonasally administered to a patient to effect anesthesia of the DnNS. Any method known in the art of anesthetizing nerves may be used to anesthetize the DnNS. Further by way of example, acupuncture techniques, application of electrical potential to a DnNS, or application of electromagnetic radiation, such as light or radio frequency radiation, to a DnNS may be used to anesthetize the DnNS. Intranasal, and preferably dorsonasal, administration of a long-acting local anesthetic pharmaceutical composition is a preferred method of inhibiting a CNvD.

Inhibition of a migraine by dorsonasal administration of at least one local anesthetic is an effective means of arresting the cascade of migraine development with consequent sterile inflammation and protracted multisystem aggravation of symptoms, particularly where such anesthesia persists for a period of at least about an hour, and preferably at least about two hours. Any of the pharmaceutical compositions described herein may be used for dorsonasal administration of the local anesthetic, using the dosages and formulations herein. As will be understood by one skilled in the art, the optimal dosage and formulation for use with an individual patient depends upon the age, size, condition, state of health, and preferences of the patient, as well as upon the identity of the local anesthetic. Selection of optimal doses and formulations are, in view of the present disclosure, well within the skill of the ordinary artisan.

Inhibition of a CNvD, a symptom of the CNvD, or both, occur very rapidly following intranasal or dorsonasal administration of a long-acting or persistent local anesthetic such as ropivacaine. Half maximal inhibition occurs within about three minutes, and the rate of rebound is negligible. Photophobia and nausea are inhibited at the same time as pain following dorsonasal administration of ropivacaine. The coincidental effect may be due to the wide ranging effects of intranasal administration of the composition of the invention on multiple subpial and cerebrovascular systems. By contrast, the migraine therapeutic effects of a serotonin receptor agonist depends on the ability of vascular flow to effect an effective concentration of the agonist at the site of the compromised cerebral blood vessels. The serotonin receptor agonists show intersubject variance in efficacy due to the biphasic nature of the relationship between the concentration of the agonist and the physiological effect in vascular structures. Serotonin receptor agonists also exhibit variable efficacy due to variable effect of individual serotonin receptor agonists upon blood vessels within the major cerebrovascular and subpial structures of a patient.

Recurring CNvDs lead to cumulative damage and neurological defects among patients afflicted with these CNvDs. For example, certain patients who are afflicted with recurring migraines sustain permanent neurological damage. Without wishing to be bound by any particular theory, it is postulated that anatomic and physiologic pathologies may be secondary to the cumulative effects of repetitive pain stimuli, pain impulses, ischemia, sterile inflammation, related processes, or some combination of these. Effective management of the neurovascular ischemic component of a recurring CNvD may decrease cumulative neurological damage attributable to the CNvD episodes. For example, ending the ischemic component of a migraine promptly after the onset of the acute migraine episode may decrease the damage and deficit exhibited in certain ophthalmic, basilar, or other migraine patients. Compromised nerve structures have a lower threshold of neuronal signaling to restart subsequent CNvD episodes. Thus, decreasing the cumulative neurological damage attributable to recurring CNvD episodes decreases the frequency with which CNvD episodes are experienced by the patient.

Further without wishing to be bound by any particular theory, the pain and other neuronal signals transmitted by cerebral nerve structures during a CNvD episode may predispose the same or other nerve structures to onset of a subsequent CNvD episode by processes analogous to "neuronal learning" or to central sensitization and amplification. Neuronal learning is a theory which has been described by others to explain the apparent self-facilitating nature of pain generation and sensation. The theory of neuronal learning postulates that the transmission of pain impulses by a particular neural pathway predisposes that particular neural pathway to future transmission of pain impulses in response to triggers or impulse-generating stimuli of lower magnitude than would normally be required for pain sensation. Noxious stimuli can also cause lasting central sensitization whereby altered sensory processes in the central nervous system amplify, even in the distant future, subsequent pain. By way of example, it has been demonstrated in surgical patients that pre-surgical central neurologic blockade (e.g. using epidural analgesia) reduces the sensation of postoperative pain in the patients, even up to more than nine weeks following surgery, relative to patients who receive identical central neurologic blockade postoperatively (Gottschalk et al., 1998, J. Amer. Med. Assoc. 279:1076–1082; Woolf et al., 1993, Anesth. Analg. 77:362–379; Shis et al., 1994, Anesthesiology 80:49–56). It is believed that failure to block transmission of pain impulses from surgically-affected sensory neurons in the postoperatively blocked patients lowers the threshold sensation needed to trigger pain impulse transmission from these neurons or facilitates central amplification of pain. In contrast, it is believed that blockade of transmission of pain impulses from the same surgically-affected sensory neurons in presurgically blockaded patients prevents this threshold-lowering effect.

While still not wishing to be bound by any particular theory, it is believed that dorsonasal administration of a long-acting or persistent local anesthetic at an early stage of a CNvD episode blocks the transmission of pain impulses from, through, or both, relevant cerebral or other neurological structures, such that these neurological structures therefore do not experience the threshold-lowering affect attributable to neuronal learning. The amount of stimulation that will induce a subsequent episode of a CNvD is thereby not lowered. Additionally, there is no central amplification of perceived pain. Because the threshold stimulation required for inducement of CNvD episodes is not lowered, and further because there is no central amplification of pain, patients treated using the compositions, kits, and methods of the invention are less predisposed to subsequent CNvD episodes, and the frequency and severity of any subsequent CNvD episodes is reduced.

Intranasal, and preferably dorsonasal, administration of a long-acting local anesthetic pharmaceutical composition can also be used to reduce the severity of an acute cerebral ischemic event, thereby decreasing neurologic deficits resulting therefrom. Without wishing to be bound by any particular theory of operation, it is believed that the following proposed mechanism explains the efficacy of this method. Tissue damage caused by an acute ischemic event is mediated by a shortage of oxygen in such tissue. This tissue damage may be alleviated in at least two ways. Damage may be alleviated by counteracting the cause of the tissue hypoxia or by inducing supplementary oxygen delivery to the tissue. Intranasal administration of a local anesthetic is believed reduce the severity of an acute cerebral ischemic event in both of these ways. It is believed that intranasal administration of a local anesthetic interrupts the neural component which contributes to the vasospasm associated with an acute cerebral ischemic event. Relief of this neural component of the event can reduce or eliminate ischemia associated with the event. Furthermore, it is believed that vasodilatory effects of intranasally administered local anesthetics cause dilation of blood vessels supplying the ischemic tissue, decreasing the degree of vessel occlusion, thereby increasing blood supply to the ischemic tissue. These vasodilatory effects may also increase blood flow through the blood vessel occlusion, for example by dilating proximal blood vessels, thereby increasing the pressure gradient across the occlusion, resulting in less watershed ischemia.

Inhibition of Muscular Headaches

Another aspect of the present invention is based on the discovery that intranasal, and preferably dorsonasal, administration of a local anesthetic to a human patient experiencing a muscular headache is sufficient to inhibit the muscular headache or a symptom associated therewith. Preferably, the local anesthetic is a long-acting or persistent local anesthetic, but shorter-acting local anesthetics are recognized as being effective to inhibit a muscular headache as well, using this method.

Prior art methods of treating a muscular headache have focused on using acetylsalicylic acid and its derivatives, non-steroidal anti-inflammatory drugs, sedatives, narcotics, and other drugs to decrease head pain, the primary symptom of muscular headaches.

What was not known, and what represents a surprising discovery, is that intranasal, and preferably dorsonasal, administration of a local anesthetic, preferably one which exhibits a duration of anesthesia equal to at least about a few minutes, is effective both to relieve head pain during the period of anesthesia and, more importantly, to inhibit a muscular headache.

Although all types of head pain, even head pain associated with diverse classes of headaches, may have similar aspects of presentation, character, or pathophysiology, muscular headaches are recognized as a separate class of headache, with distinct characteristics (Headache Classification Committee of the International Headache Society, 1988, Cephalalgia 8(Suppl. 7):19–28).

It has not previously been recognized that local anesthetics, when administered intranasally or dorsonasally, were capable of relieving muscular headache pain or muscle spasm associated with muscular headaches.

The present invention also includes a method of inhibiting a muscular headache episode in a human patient, the method comprising intranasally, and preferably dorsonasally, administering to the patient a composition comprising a local anesthetic and an analgesic or other pharmaceutically active agent. Preferably, the local anesthetic is not cocaine, and administration of the composition results in relief of a symptom of the muscular headache and further results in improved delivery of the analgesic or other agent to a cerebral neurovascular tissue of the patient. By way of example, the agent may be aspirin, acetaminophen, a non-steroidal anti-inflammatory drug, a tricyclic antidepressant, an anxiolytic, a serotonin agonist such as a triptan or a chroman compound, a narcotic, or a drug that increases cerebral levels of γ-aminobutyric acid. Compounds, formulations, and dosages of analgesics and other pharmaceutically active agents described in this method are known in the art. Owing, in part, to the vasodilatory activity of local anesthetics, these compounds may be used according to this method at doses of about half their art-recognized doses to their full art-recognized doses.

The method described herein for treating a muscular headache episode can also be used to prevent such an episode. Certain muscular headaches can be reliably predicted to occur following particular patient activities prior to the onset of the episode. By treating a patient using the method described herein for treating a muscular headache episode at a time when the episode is expected, at a time when the patient is under emotional distress, or at a time when the patient is exposed to another headache-triggering condition, the muscular headache episode may be prevented.

It is believed that the compositions and methods of the invention provide more rapid and complete relief of muscular headache symptoms than do known compositions and methods. Furthermore, intranasal and dorsonasal administration of local anesthetics are not associated with the side effects known to be associated with prior art headache treatments, and do not induce tolerance, as do prior art headache treatments. Thus, besides being a useful headache treatment in itself, the method of the invention is a useful alternative or adjunctive therapeutic modality with regard to prior art muscular headache treatments.

Theory Proposed to Explain the Efficacy of the Compositions and Methods of the Invention for Inhibiting a Muscular Headache It should be appreciated that the superiority of the compositions and methods of the invention relative to the compositions and methods of the prior art does not depend upon the accuracy of the theory offered to explain the superior results. Regardless of the mechanism by which muscular headaches are generated, intranasal, and preferably dorsonasal, administration of a local anesthetic, preferably a long-acting or persistent local anesthetic, inhibits a muscular headache.

Without wishing to be bound by any particular theory, it is believed that the following model explains the physiological processes underlying a muscular headache. It is believed that non-desirable sustained muscle contraction is related to local pathology, central influences and multisynaptic modulation, and involves gamma efferent neuronal muscle spindle activation. Related monosynaptic conduction through the ventral horn augments both efferent neuronal discharge and muscle contraction. A muscular headache cycle of pain, muscle spasm, local chemical changes, neuronal excitability or hyperexcitability, skeletal muscle blood vessel compression or spasm, and anxiety ensues.

Anesthesia of a DnNS such as the SPG effected by dorsonasal delivery of a topical anesthetic is an effective means of inhibiting a chronic muscular headache, particularly where such anesthesia persists for a period of at least about an hour, and preferably at least about two hours. Anesthesia of the DnNS and consequent relief of associated symptoms occurs very rapidly following intranasal or dorsonasal administration of a long-acting or persistent local anesthetic such as ropivacaine. Half maximal arrest occurs within about three minutes. The effect may be due to the wide ranging effects of DnNS anesthesia on multiple subpial and cerebrovascular systems. For example, the trigeminal nerve is in communication with upper cervical nerves, particularly cervical nerve 2. Interruption of efferent or afferent limbs of cervical nerve 2 would inhibit facial and scalp skeletal muscle spasm, thereby breaking a major component of the muscular headache cycle.

Anesthesia of a DnNS such as the SPG for a period of at least about a few minutes, preferably at least about one hour, and more preferably at least about two hours, may be achieved in any of a number of ways. For example, a shorter-acting local anesthetic may be intranasally or dorsonasally administered to a patient to effect anesthesia of the DnNS for a period of less than about one hour, it being understood that such treatment may be effective only to alleviate a muscular headache episode, possibly without inhibiting the episode. Also by way of example, a long-acting or persistent local anesthetic may be intranasally or dorsonasally administered to a patient to effect anesthesia of the DnNS. Further by way of example, a sustained release formulation of a shorter-acting, long-acting, or persistent local anesthetic may be dorsonasally administered to a patient to effect anesthesia of the DnNS. Any method known in the art of anesthetizing nerves may be used to anesthetize the DnNS. Further by way of example, acupuncture techniques, application of electrical potential to a DnNS, or application of electromagnetic radiation, such as light or radio frequency radiation, to a DnNS may be used to anesthetize the DnNS.

Local Anesthetics

The chemical identity of the local anesthetic or anesthetics used in the compositions and methods of the invention is not critical. As described herein, long-acting or persistent local anesthetics may be administered in pharmaceutically acceptable carriers, and shorter-acting local anesthetics may be administered in sustained release formulations or in conjunction with an additional compound which extends their anesthetic effect.

Compounds having local anesthetic activity which may be used to practice the invention include, but are not limited to, ambucaine, amolanone, amylocaine, benoxinate, betoxycaine, biphenamine, bupivacaine, levo-bupivacaine, butacaine, butamben, butanilicicaine, butethamine, butoxycaine, carticaine, 2-chloroprocaine, cocaethylene, cocaine, cyclomethycaine, dibucaine, dimethisoquin, dimethocaine, diperodon, dyclonine, ecgonidine, ecgonine, ethyl aminobenzoate, ethyl chloride, etidocaine, levo-etidocaine, dextro-etidocaine, β-eucaine, euprocin, fenalcomine, fomocaine, hexylcaine, hydroxyprocaine, hydroxytetracaine, isobutyl p-aminobenzoate, leucinocaine mesylate, levoxadrol, lidocaine, lidocaine salicylate monohydrate, meperidine, mepivacaine, levo-mepivacaine, meprylcaine, metabutoxycaine, methyl chloride, myrtecaine, naepaine, octacaine, orthocaine, oxethazaine, parethoxycaine, phenacaine, phenol, pipecoloxylidides, piperocaine, piridocaine, polidocanol, pramoxine, prilocaine, procaine, propanocaine, proparacaine, propipocaine, propoxycaine, pseudococaine, pyrrocaine, quinine urea, risocaine, ropivacaine, levo-ropivacaine, salicyl alcohol, sameridine, tetracaine, tolycaine, trimecaine, veratridine, and zolamine, as well as 2-alkyl-2-alkylamino-2',6'-acetoxylidide compounds, such as those described in U.S. Pat. No. 3,862,321; glycerol 1,2-bis-aminoalkyl ether compounds, such as those described in U.S. Pat. No. 4,117,160; benzisoxazole compounds, such as those described in U.S. Pat. No. 4,217,349; O-aminoalkylsalicylate compounds, such as those described in U.S. Pat. No. 4,298,603; heterocyclic phenoxyamine compounds, such as those described in U.S. Pat. No. 4,379,161; 2-and 3-aryl substituted imidazo(1,2-A) pyridine compounds, such as those described in U.S. Pat. No. 4,871,745, in U.S. Pat. No. 4,833,149, and in U.S. Pat. No. 4,727,145; polyorganophosphazene compounds, such as those described in U.S. Pat. No. 4,495,174 and in U.S. Pat. No. 4,636,387; tertiary-alkylamino-lower acyl-xylidide compounds, such as those described in U.S. Pat. No. 3,925,469; amidinourea compounds, such as those described in U.S. Pat. No. 4,147,804; 3-(5'-adenylates) of lincomycin-type or clindamycin-type compounds, such as those described in U.S. Pat. No. 4,397,845; N-substituted derivatives of 1-(4'-alkylsulfonylphenyl)-2-amino-1,3-propanediol compounds, such as those described in U.S. Pat. No. 4,632,940; tertiary aminoalkoxyphenyl ether compounds, such as those described in U.S. Pat. No. 4,073,917; adenosine compounds, such as adenosine and adenosine mono-, di-, and triphosphate; lauryl polyglycol ether compounds, such as those described in U.S. Pat. No. 5,676,955 and mixtures of such ether compounds; 2-(ω-alkylaminoalkyl)-3-(4-substituted-benzylidene)phthalimidine compounds or 2-(ω)-dialkylaminoalkyl)-3-(4-substituted-benzylidene) phthalimidine compounds, such as those described in U.S. Pat. No. 4,551,453; N,N,N-triethyl-N-alkyl ammonium salts, such as those described in U.S. Pat. No. 4,352,820; L-N-n-propylpipecolic acid-2,6-xylidide compounds, such as those described in U.S. Pat. No. 4,695,576; N-substituted 4-piperidinecarboxamide compounds, such as those described in U.S. Pat. No. 5,756,520; N-substituted 4-phenyl-4-piperidinecarboxamide compounds, such as those described in U.S. Pat. No. 5,360,805; polymers comprising repeating units of one or more local anesthetic moieties, such as polymers described in U.S. Pat. No. 3,914,283; compounds of formula (I):

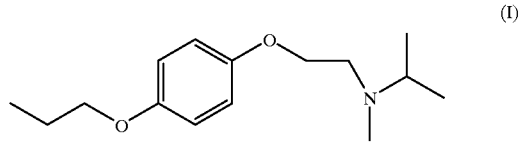

(I)

and its derivatives, such as those described in International Patent Application Publication No. WO 97/38675; compounds of formula (II):

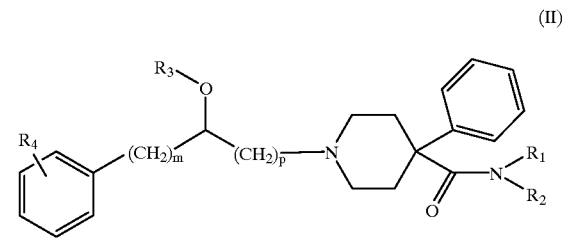

(II)

wherein $R_{1-14}$, m, and P are defined as in International Patent Application Publication No. WO 95/21821; ester forms of any of these compounds, salts of any of these compounds, compounds otherwise chemically related to one of these compounds which would be effective in the present invention, and sustained release preparations of any of these agents, as described herein. Also included are derivatives of the foregoing, where the derivative is any chemically related compound effective for the present invention.

Synonyms, including chemical names, chemical formula, and trade names, for many of the local anesthetics described herein may be found in Physician's Desk Reference® (Medical Economics Co., Inc., Montvale, N.J. 51st ed., 1997) or in PDR® Generics™ (Medical Economics Co., Inc., Montvale, N.J. 2nd ed., 1996).

The local anesthetic is preferably selected from the group consisting of bupivacaine, levo-bupivacaine, ropivacaine, levo-ropivacaine, tetracaine, etidocaine, levo-etidocaine, dextro-etidocaine, and levo-mepivacaine.

Local anesthetics including, but not limited to, bupivacaine and ropivacaine, which are related to aminoacyl local anesthetics exhibit intrinsic vasoactive effects on cerebral blood vessel tone and reduce pain sensitivity locally. When administered dorsonasally, these compounds are believed to effect anesthesia of the SPG and other DnNSs, which results in increased volumetric flow of blood in cerebral blood vessels and reduces inflammation initiated by functional ischemia. It is understood that the S(levo)-enantiomer of ropivacaine and the S(levo)-enantiomer of bupivacaine exhibit lower physiological toxicity and better sensory blocking properties than the corresponding R(dextro)-enantiomers. The S(levo)-enantiomer of ropivacaine is preferred for use in the compositions and methods of the invention, as are the S(levo)-enantiomers of bupivacaine, etidocaine, and mepivacaine.

Ropivacaine exhibits lower cardiovascular and central nervous system toxicity than bupivacaine. Compared with bupivacaine, ropivacaine blocks nerve fibers, such as Aδ and C sensory fibers, more preferentially than other neurons such as motor neurons (Rosenberg et al., 1986, Br. J. Anaesth. 55:163–167). Thus, ropivacaine is preferred over bupivacaine in the compositions, kits, and methods of the invention.

For local anesthetics which have a chiral center, the local anesthetic may be a single optical isomer of the local anesthetic, a racemic mixture of the optical isomers, or some other mixture of optical isomers. By way of example, a 90:10, a 80:20, a 70:30, or a 50:50 ratio, by weight or by molecule number, of one optical isomer to the other may be used.

It is understood by the inventor that the potency of anesthesia effected by local administration of an aryl-2-piperidinecarboxamide derivative such as bupivacaine, ropivacaine, or lidocaine may be increased by increasing the lipid solubility of the derivative. This may be achieved, for example, by increasing the lipophilic character of substituent of the piperidyl nitrogen atom. The partition coefficient of ropivacaine (in an n-heptane/buffer biphasic system) is about 2.9 times greater than the partition coefficient of lidocaine (Rosenberg et al., 1986, Br. J. Anaesth. 58:310–314). The partition coefficient of bupivacaine is about 10 times greater than the partition coefficient of lidocaine (Id.). As described herein, ropivacaine and bupivacaine are long-acting local anesthetics, while lidocaine is not a long-acting local anesthetic. Thus, a way in which a skilled artisan may determine whether a particular local anesthetic is a long-acting local anesthetic is to determine whether the partition coefficient of the local anesthetic in an n-heptane/aqueous biphasic system is greater than the partition coefficient of lidocaine in such a system. If the partition coefficient of the particular local anesthetic is greater than the partition coefficient of lidocaine, then the particular local anesthetic is likely a long-acting local anesthetic. Preferably, the partition coefficient of the particular local anesthetic is at least 2.9 times greater than the partition coefficient of lidocaine. The potency of anesthesia of a local anesthetic may be increased by modifying the chemical structure of the local anesthetic in such a manner as to increase the partition coefficient of the local anesthetic, for example by adding hydrophobic substituents to the local anesthetic molecule or lengthening hydrophobic substituents of the local anesthetic. Preferably, the local anesthetic used in the compositions, kits, and methods of the present invention has a partition coefficient in an n-heptane/aqueous biphasic system greater than the partition coefficient of lidocaine in such a system.

It is understood by the inventor that the duration of anesthesia effected by local administration of an anesthetic such as an aryl-2-piperadinecarboxamide derivative is related to the proportion of the anesthetic which is bound to protein in vivo. Approximately 95% of each of bupivacaine and ropivacaine is bound to protein in vivo, while only about 65% of lidocaine is bound to protein in vivo. Thus, another way in which a skilled artisan may determine whether a particular local anesthetic is a long-acting local anesthetic is to determine whether the proportion of the particular local anesthetic which is bound to protein in vivo is greater than the proportion of lidocaine which is bound to protein in vivo. If the proportion of the particular local anesthetic which is bound to protein in vivo is greater than the proportion of lidocaine which is bound to protein in vivo, then the particular local anesthetic is likely a long-acting local anesthetic. The proportion of the local anesthetic used in the compositions, kits, and methods of the present invention which is bound to protein in vivo should be greater than about 65%. Preferably, the proportion of the particular local anesthetic which is bound to protein in vivo is at least about 95%.

The duration of anesthesia of a local anesthetic may be increased by modifying the chemical structure of the local anesthetic in such a manner as to increase the proportion of the particular local anesthetic which is bound to protein in vivo, for example by adding chemical substituents to the particular local anesthetic molecule which are capable of binding, covalently or non-covalently, to protein moieties.

The therapeutic effects of local anesthetics in the present invention are not directly proportional to their prior art use elsewhere in the body as local anesthetics. Thus, the duration and pain-relieving effects of the long-acting and persistent local anesthetics in the present invention are enhanced, compared to their use as local anesthetics elsewhere in the body. The enhanced duration and pain-relieving effects of the long-acting and persistent local anesthetics of the present invention are surprising, compared with the effects achieved using other methods of using local anesthetics.

For example, administration of ropivacaine may anesthetize a nerve structure for a period about 1.5 to about 4 times that achieved by administration of lidocaine, depending on the location and type of the nerve structure, and further depending on the concentration and total dose of the local anesthetic and on the presence of vasoconstrictors or other drugs which affect either uptake of the local anesthetic by the nerve structure or clearance of the local anesthetic from the anatomical site of the nerve structure. The difference between the period of anesthesia effected by administration of ropivacaine and the period of anesthesia effected by administration of lidocaine is less pronounced when the site of administration is a skin or mucosal surface. Thus, one would expect that if lidocaine and ropivacaine affected CNvDs and their symptoms by the same mechanism, administration of ropivacaine to a patient afflicted with a CNvD would provide relief lasting no more than about 4 times as long as the relief provided by administration of lidocaine, and probably closer to no more than about 1.5 times as long. In fact, as described herein, the relief provided by administration of ropivacaine to CNvD patients, such as migraine patients, persisted far longer than the duration of relief provided by administration of lidocaine to such patients. This surprising result further highlights the difference between prior art methods of relieving a symptom of a CNvD and the methods of the invention for inhibiting a CNvD.

Dosing Information

The following dosing information is believed to be useful for the CNvD-inhibiting methods and the muscular headache inhibiting methods of the invention. Dosing information relevant to the systemic drug delivery method of the invention is described separately in the portion of the present disclosure which describes that method.

Various dosage forms may be made which comprise a local anesthetic at a concentration of about 0.01% to about 53% by weight, preferably a concentration of about 0.25% to about 10% by weight, more preferably about 0.5% to about 5% by weight, and even more preferably at about 2.5% by weight. The pharmaceutical composition should be formulated to deliver about 10 micrograms to about 2.5 grams of the local anesthetic to each nostril of a patient, and preferably to deliver about 10 micrograms to about 1 gram. Unit dosage forms containing an amount of the pharmaceutical composition in these ranges may be used. When the pharmaceutical composition is in the form of a liquid for topical application (e.g. a spray), a dose of the pharmaceutical composition may be contained, for example in a volume of about 10 microliters to about 5 milliliters, and preferably in a volume of about 100 microliters to about 3 milliliters, for delivery to each nostril. Such liquid pharmaceutical compositions preferably contain the local anesthetic at a concentration of about 0.01% to about 20% (w/v), more preferably about 0.25% to about 5% (w/v). When the pharmaceutical composition is in the form of a solid, semi-solid, gel, emulsion, or the like, the pharmaceutical composition may be formulated to contain about 10 micrograms to about 2.5 grams of the local anesthetic to the patient per nostril in a volume of about 10 microliters to about 5 milliliters. The concentration of the local anesthetic in the solid, semi-solid, gel, or emulsion form is preferably about 0.01% to about 53% (w/w), more preferably about 0.1% to about 20% (w/w).

A bulk form of a long-acting local anesthetic pharmaceutical composition may be made and administered to a patient in one or more doses which comprise the dosage amounts described in the preceding paragraph.

Pharmaceutical Compositions

The long-acting local anesthetic pharmaceutical composition that is useful in the methods of the invention may be intranasally or dorsonasally administered in a variety of formulations that can be made readily by one of skill in the art of pharmacology in view of the present disclosure. Formulations which are useful for intranasal administration of the pharmaceutical composition of the invention include, but are not limited to, jelly, creme, gel, semi-solid, emulsion, sol-gel, foam, a eutectic mixture, liquid, droplet, aerosol, powder, microsomes, liposome, sustained release, degradable polymer, polymer microspheres, impregnated film, fiber, or patch, coated film, fiber, or patch, and other similar dosage forms. The pharmaceutical composition of the invention may contain one or more than one local anesthetic agent. When the pharmaceutical composition contains more than one local anesthetic agent, the agents may be mixed in substantially any ratio such as, for example, a eutectic ratio as described in U.S. Pat. No. 4,562,060.

In addition to the local anesthetic, such pharmaceutical compositions may contain pharmaceutically acceptable carriers and other ingredients known to enhance and facilitate drug administration with the additional pharmaceutical agents disclosed herein. Compounds, formulations, and dosages of the additional pharmaceutically active agents described in this method are known in the art. Owing, in part, to the vasodilatory activity of local anesthetics, these compounds may be used according to this method at doses of about half their art-recognized doses to their full art-recognized doses.

Such pharmaceutical compositions may also contain ingredients to enhance sensory acceptability of the composition to a human patient, such as aromatic, aromatherapeutic, or pleasant-tasting substances. The pharmaceutical compositions may also, for example, be made in the form of a flexible solid or semisolid carrier comprising the local anesthetic, such as one of the carriers described in U.S. Pat. No. 5,332,576 or in U.S. Pat. No. 5,234,957; or in the form of suspended microspheres, such as those described in U.S. Pat. No. 5,227,165. Solid and semi-solid formulations of a shorter-acting, a long-acting, or a persistent local anesthetic are preferred in the compositions, methods, and kits of the inventions, because such preparations improve local anesthetic localization. In these forms, there is less dilution of the local anesthetic by body fluids and less transport of the local anesthetic to an unintended body location. Furthermore, it is believed that these formulations will reduce or minimize unintended side effects such as disagreeable taste, oropharyngeal numbness, dysphasia, and compromise of protective reflexes. In these formulations, a lower amount of local anesthetic may be used, relative to other formulations.

Numerous pharmaceutically acceptable carriers are known in the art, as are methods of combining such carriers with local anesthetics. Examples of such carriers and methods are described, for example, in Genaro, ed., 1985, *Remington's Pharmaceutical Sciences*, Mack Publishing Co., Easton, Pa.

It is understood that the pharmaceutical composition of the invention may comprise a combination of any of the forms described herein. By way of example, microparticles, microsomes, or liposomes comprising a local anesthetic may be suspended in a solution or other formulation of the same or a different local anesthetic, whereby the solution or other formulation provides a rapid onset of anesthesia and the local anesthetic in the form of microparticles, microsomes, or liposomes provides a sustained duration of anesthesia. Sustained release preparations may comprise a slowly-released formulation of a local anesthetic. Inclusion of another local anesthetic in such formulations, in a free or salt (i.e., not slowly-released) form confers to the formulation the ability to act both with a rapid onset of anesthesia and a sustained duration of anesthesia. All such combinations of formulations described herein are included in the invention.

The long-acting local anesthetic pharmaceutical composition useful for practicing the invention must be administered in a dose sufficient to inhibit the CNvD for at least about one hour, and preferably for at least about two hours. Doses of the long-acting local anesthetic pharmaceutical composition may be administered in a single dose, in multiple doses, in sustained release doses, or continuously.

The local anesthetic(s) may be present in the pharmaceutical composition at any concentration from a very dilute concentration through the solubility limit of the local anesthetic in the medium in which it is delivered. The local anesthetic(s) may also be present at a concentration greater than the solubility limit of the local anesthetic in the medium in which it is delivered by using a crystalline, microcrystalline, or amorphous solid form of the local anesthetic, preferably suspended in a gel, creme, liquid, liposome, microsome, solid polymeric matrix, or the like. In various embodiments, the local anesthetic may be administered in the form of a eutectic mixture of local anesthetics, such as described in U.S. Pat. 4,562,060, in the form of encapsulated or embedded local anesthetic, such as described in U.S. Pat. 5,085,868, in the form of an oil-in-water emulsion, such as described in U.S. Pat. No. 5,660,837, or in the form of an emulsion, a creme, a eutectic mixture, or a microemulsion, such as described in International Patent Application Publication No. WO 97/38675, particularly one having thermoreversible gelling properties. Because the nasal cavity is normally cooler than gum pockets, the environment disclosed in International Patent Application Publication No. WO 97/38675, a composition having thermoreversible gelling properties, wherein the composition is a fluid at about 20° C. and a gel or semi-solid at the cooler temperature in the human nasal cavity (i.e., about 30–37° C.), is preferred. Any of these compositions may be conveniently delivered dorsonasally and, once so delivered, will be available where placed within the nasal cavity for a sustained period after administration and will spread or drip into other tissues to a lesser degree than would a liquid composition. By using one of these formulations, less of the active compound yields greater therapeutic results and has significantly decreased side effects, such as local and systemic toxicity, tongue and oropharyngeal numbness, discomfort, bad taste, dysphasia, and possible compromise of protective airway reflexes.

Other possible formulations may be made by of one of skill in the art of pharmacology in view of this disclosure without departing from the spirit of the invention. See, for example, (Genaro, ed., 1985, Remington's Pharmaceutical Sciences, Mack Publishing Co., Easton, Pa.) for a number of forms of typical pharmaceutical compositions that may be adapted readily to the present invention in view of this disclosure.

Co-Administration of a Local Anesthetic with Another Migraine or Muscular Headache Therapeutic Agent Numerous pharmaceutically active agents are thought to exhibit their limited therapeutic activity by virtue of the ability of the agent to interact with one or more receptors present on the surface of cerebral blood vessels or other structures. By way of example, migraine therapeutic agents known as serotonin receptor agonists include such agents as sumatriptan and zolmitriptan, and are believed to interact with serotonin receptors. In order to exhibit their pharmacological effects, such agents must gain access by systemic vascular delivery to cerebral blood vessels which have altered vascular flow during an acute migraine episode (Scott, 1994, Clin. Pharmacokinet. 27:337–344) and must achieve a critical concentration at the cerebrovascular location of the corresponding receptor(s) in the compromised area. Thus, these pharmaceutically active agents must be administered at the onset of an acute migraine episode in order to avoid the cascade of inflammation that follows initiation of the episode (Limmroth et al., 1996, Curr. Opin. Neurol. 9:206–210). -Following delivery of one of these agents to the compromised area of a cerebral blood vessel, the concentration of the drug gradually decreases at those sites, and rebound can occur.

Topical local anesthetics are vasodilators and therefore inhibit vasoconstriction, with the exceptions of cocaine, which is a vasoconstrictor. It is believed that the vasodilatory effects of topical local anesthetic administration results from both a direct effect of the anesthetic upon the affected blood vessel and from an indirect effect of the anesthetic upon nerve structures associated with the blood vessel.

In normal states, most blood vessels, particularly those of smaller diameter, do not transport blood because they are not open, due to constriction of blood vessels located proximal thereto with respect to the heart or due to increased muscle tone in the blood vessel wall itself. Should these vessels open at once, profound hypotension would develop immediately, resulting in shock. Many and complex mechanisms are involved in the regulation of blood vessel tone and blood circulation. Hence, in any given tissue or organ, many blood vessels are closed. Blood vessel recruitment refers to a process whereby closed or partially constricted blood vessels are opened or dilated. This increases the number and surface area of blood vessels available for uptake and allows greater blood flow through these vessels. The latter mechanism increases drug transport away, and this decreases local blood drug concentration, favoring drug diffusion into the blood. All of these mechanisms increase drug uptake and transport. Surface vasodilation effected by an intranasally or dorsonasally administered local anesthetic other than cocaine promotes greater blood vessel recruitment and therefore, greater systemic uptake of the pharmaceutically active agent administered in conjunction with the local anesthetic. Hence, co-administration of a local anesthetic and a pharmaceutically active agent results in a more rapid and greater systemic uptake of the pharmaceutically active agent. This produces a more rapid and greater concentration of the pharmaceutically active agent at the affected site.

Furthermore, vasodilation of arterial structures which pass through the intranasal mucosa to feed other relevant neural structures will result in increased delivery of intranasally administered pharmaceutically active agents directly to target sites, especially if arterial blood flows through an area to which the agent and anesthetic are administered. For example, the sphenopalatine artery provides blood supply to much of the middle turbinate of the human nose, to the region of the nasal epithelium overlying the SPG, and to the SPG. Without wishing to be bound by any particular theory, it is believed that the anesthetizing effect of local anesthetics such as bupivacaine induces vasodilation of arterial structures coursing through local tissue on the way to the brain and other relevant neural structures, and increases agent delivery. Additionally, the decreased extracranial and intracranial vasospasm and vasodilation which result from anesthesia of the SPG increases blood flow to relevant structures and therefore increases drug delivery to relevant tissues even further. Hence, intranasal administration of local anesthetic (s) induces both local and intracranial vasodilation and decreases or prevents vasoconstriction caused by normal autoregulatory processes, by neurally mediated processes, or by release of neurotransmitters, neuropeptides, or other factors which are associated with an acute CNvD or muscular headache. Thus, administration of a local anesthetic to the region of the nasal epithelium overlying the SPG and to other regions of the epithelium located nearby facilitates transport of a pharmaceutically active agent from the surface of the nasal epithelium directly into relevant venous, capillary, and arterial vessels and into the general systemic circulation where intracranial vasodilation or decreased vasospasm results in increased active agent delivery to sites at which it exhibits its pharmaceutical activity.

Therefore, it is anticipated that dorsonasal delivery of a composition which comprises a long-acting or persistent local anesthetic and a pharmaceutically active agent will result in greater local delivery of the agent to a cerebral neurovascular tissue than could be achieved by dorsonasal delivery of the agent alone.

Furthermore, if agents, such as sumatriptan and ropivacaine, for example, are believed to have different mechanisms of action, it is believed that the therapeutic effects of the two compounds will be pharmacodynamically synergistic, or at least additive. This is yet another manner that co-administration of a local anesthetic and another pharmaceutical agent is advantageous.

Without wishing to be bound by any particular theory of operation, it is believed that the co-administered compositions inhibit the headache and diminish the likelihood that the headache will rebound or recur. This is believed to be especially true for patients who are afflicted with a plurality of distinct headaches or patients who experience separate headache triggers in series.

The present invention includes a method of inhibiting a neurovascular or muscular headache in a human patient, the method comprising intranasally, and preferably dorsonasally, administering to the patient a composition comprising at least one local anesthetic and a pharmaceutically active agent effective for treatment of the headache. Preferably, the local anesthetic is a long-acting local anesthetic, a persistent local anesthetic, or a sustained release formulation of a local anesthetic other than cocaine, whereby intranasal, and preferably dorsonasal, administration of the composition results in improved uptake of the pharmaceutically active agent by a cerebral neurovascular tissue of the patient and to enhancement of the pharmaceutical activity of the agent.

By way of example, when the headache is a migraine, compositions for inhibiting the migraine and co-administering a migraine therapeutic agent include a sustained release formulation of a composition comprising sumatriptan (e.g. Imitrex™, Glaxo-Wellcome Inc., Research Triangle, NC) and lidocaine, a composition comprising zolmitriptan (e.g. Zomig™, Zeneca Pharmaceuticals, Wilmington, Del.) and bupivacaine, a composition comprising rizatriptan (e.g. Maxalt™, Merck & Co., West Point, Pa.) and ropivacaine, a composition comprising naratriptan (e.g. Naramig™, Glaxo-Wellcome Inc., Research Triangle, NC) and tetracaine, and a composition comprising a beta blocker and etidocaine.

Further by way of example, when the headache is a muscular headache, compositions for inhibiting the muscular headache and co-administering a muscular headache therapeutic agent include compositions comprising a local anesthetic ingredient selected from the group consisting of a persistent local anesthetic, a long-acting local anesthetic, and a sustained release formulation of a local anesthetic and an additional pharmaceutically active agent selected from the group consisting of a vasoconstrictor, epinephrine, norepinephrine, phenylephrine, methysergide, propanolol, a calcium channel blocker, verapamil, ergot, an ergotamine preparation, dihydroergotamine, a serotonin agonist, sumatriptan, zolmitriptan, rizatriptan, naratriptan, a chroman compound, aspirin, acetaminophen, a non-steroidal anti-inflammatory drug, caffeine, a narcotic, butorphanol tartrate, meperidine, a mast cell degranulation inhibitor, cromolyn sodium, eucalyptol, tetrodotoxin, desoxytetrodotoxin, saxitoxin, an organic acid, a sulfite salt, an acid salt, a glucocorticoid compound, a steroid ester, magnesium or lithium ions, a centrally-acting analgesic, a beta blocker, an agent that increases cerebral levels of γ-aminobutyric acid, butalbital, a benzodiazepine, valproat, gabapentin, divalproex sodium, a tri-cyclic antidepressant, a narcotic analgesic, an oral muscle relaxant, a tranquilizer, a muscle relaxant, and another compound.

The local anesthetic compounds, formulations, dosages, and methods of administration which are useful for this method of the invention are substantially the same as those described herein with respect to inhibiting a neurovascular headache, a muscular headache, or a CNvD. Compounds, formulations, and dosages of the other pharmaceutically active agents described in this method are known in the art. Owing, in part, to the vasodilatory activity of local anesthetics, these compounds may be used according to this method at doses of about half their art-recognized doses to their full art-recognized doses.

The composition may comprise a local anesthetic and a pharmaceutically active agent which is effective for treating a CNvD or a muscular headache. By way of example, such a composition may comprise ropivacaine and an additional ingredient. The additional ingredient may, for example, be a serotonin receptor agonist, including, but not limited-to, a triptan, e.g. sumatriptan or a chroman compound such as one of the compounds described in U.S. Pat. Nos. 5,387,587; 5,420,151; 5,639,772; and 5,656,657, a non-steroidal anti-inflammatory drug, an anti-emetic, or a mast cell degranulation inhibitor such as cromolyn sodium.

In addition, the composition may comprise an agent which increases or prolongs either or both of the anesthetic effect and the tissue uptake of the local anesthetic. Such agents include, for example, an n-glycofurol compound, such as one of the compounds described in U.S. Pat. No. 5,428,006, eucalyptol, a toxin such as tetrodotoxin, desoxytetrodotoxin, or saxitoxin, an organic acid, a sulfite salt, an acid salt, magnesium or lithium ions, and a centrally-acting analgesic.

In addition, the composition may be a combination of a beta blocker and a local anesthetic, as described, for example, in European Patent No. 754060. The agent may also be a drug that increases cerebral levels of γ-aminobutyric acid (GABA), either by increasing GABA synthesis or decreasing GABA breakdown. Such GABA-affecting agents include, for example, butalbital, benzodiazepines, valproat, gabapentin, and divalproex sodium. The agent may also be an agent effective for treatment or prevention of neurodegenerative disorders such as, for example, (S)-α-phenyl-2-pyridineethanamine(S)-malate, as described in European Patent No. 970813. Furthermore, the agent may be a compound which decreases inflammation, including, for example, a glucocorticoid compound such as a steroid ester. Compounds, formulations, and dosages of vasoconstrictors and other pharmaceutically active agents described in this method are known in the art. Owing, in part, to the vasodilatory activity of local anesthetics, each of these compounds may be used according to this method at doses of about half their art-recognized doses to their full art-recognized doses.

In a patient refractory to monotherapy or treatment using a local anesthetic composition comprising only one additional compound, the composition may be combined with one, two, or more additional compounds, and this combined composition may prove to have therapeutic effects which are synergistic, or at least additive, with respect to each of the individual ingredients. By way of example, such a combined composition may comprise a long-acting or persistent local anesthetic, a beta-blocker, and a serotonin receptor agonist.

Methods of Effecting Intranasal or Dorsonasal Administration

Intranasal administration of a composition may be effected by any method by which the composition is provided to any portion of the nasal epithelium. Intranasal administration of a composition comprising a local anesthetic according to certain methods of the invention is preferably effected by dorsonasal administration of the local anesthetic.

Dorsonasal administration of a pharmaceutical composition may be effected by any method or route which results in delivery of the composition to a tissue, fluid, or surface of a human, whereby a component of the composition is provided to a DnNS either directly or by diffusion through tissue or fluid interposed between the DnNS and the site of administration. For example, dorsonasal administration of a composition comprising a local anesthetic may be effected by injecting a composition directly into a DnNS or by topically applying the composition to a tissue located in close anatomic proximity to the SPG, whereby the local anesthetic is capable of diffusing from the tissue to a DnNS such as the SPG. Topical dorsonasal administration may be accomplished by an intranasal route or by an oropharyngeal route, for example. As described herein, nasal drip methods, nasal spray application methods, and mechanical application methods may be used to effect topical dorsonasal administration of a composition comprising a local anesthetic.

Intranasal administration of the composition of the invention may be improved if the nasal cavity is rinsed, treated with a decongestant, or otherwise cleared of material which might impede intranasal delivery prior to administration of the composition.

As described herein in Example 1, dorsonasal administration of ropivacaine to patients afflicted with migraine using an intranasal spray method, an intranasal drip method, or an intranasal cotton swab method yielded different response rates and different values for the efficacy of ropivacaine for relief of migraine. Although drip and spray methods resulted in wider ropivacaine distribution within the nasal cavity, direct application of ropivacaine to the region of the nasal epithelium overlying the SPG using a cotton swab yielded the most rapid and most effective inhibition of migraine.

The pharmaceutical composition that is useful in the methods of the invention may be administered topically in the types of formulations noted herein. Intranasal, and preferably dorsonasal, administration of the composition may be achieved by providing a mist or aerosol spray comprising the composition to the nasal cavity via the nostril, by providing drops or a stream of liquid comprising the composition to the nasal cavity via the nostril or by injection of the liquid using a hypodermic needle which penetrates the facial skin of the patient, by directly applying the composition dorsonasally using a flexible or anatomically-shaped applicator inserted through the nose or mouth of the patient, including an applicator or implant which is left in place over a period of time, by introducing into the nasal cavity a liquid, gel, semi-solid, powder, or foam comprising the composition, or by any other means known to one of skill in the art of pharmaceutical delivery in view of this disclosure.

Intranasal, and preferably dorsonasal, administration of a pharmaceutical composition to a human has distinct advantages relative to other routes of administration. By administering a composition intranasally or dorsonasally, a high local concentration of the composition in a relevant neural structure, and possibly in the cerebral neurovasculature, may be achieved relative to the systemic concentration of the composition. Local delivery is advantageous in situations in which systemic exposure to the composition is undesirable, either because the composition is metabolized systemically or because systemic exposure results in harmful symptoms. By way of example, systemic administration of a local anesthetic such as bupivacaine is undesirable because bupivacaine is metabolized in the liver and because systemic administration of a relatively large amount of bupivacaine is known to cause serious adverse effects.

Another advantage of intranasal or dorsonasal administration of a compound, at least where local cerebral neurovascular delivery is desired, is that a lesser amount of drug may be administered than would be necessary to administer via a different route. Absorption of intranasally or dorsonasally delivered drug into cerebral neurovascular tissue enables the patient to avoid digestive or at least some hepatic drug metabolism which could occur, for instance, if the drug were administered orally. Furthermore, intranasal or dorsonasal delivery of a drug requires less intensive intervention by a medical professional than some other delivery methods, such as intravenous delivery. Self-medication by an intranasal or dorsonasal route is practical, as evidenced by the many nasal and pulmonary delivery devices and drug formulations which are commercially available.

DnNSs may not be directly accessible via the nasal cavity. However, because of the anatomic proximity of DnNSs to the nasal epithelium, anesthesia of a DnNS can be effected by topical administration of a local anesthetic to the region of the nasal epithelium overlying the SPG or to the region of the nasal epithelium near that region. For example, within the nasal cavity, the SPG lies dorsal to the posterior tip of the middle concha, and is covered by the nasal epithelium at a variable depth of one to nine millimeters (Sluder, 1908, N.Y. State J. Med. 27:8–13; Sluder, 1909, N. Y. State J. Med. 28:293–298). Thus, a compound applied to the surface of the nasal epithelium at or near the region of the nasal epithelium overlying the SPG, such as the surface of the nasal epithelium dorsal to the posterior tip of the middle concha can diffuse through the epithelium and any intervening tissue or fluid to reach the SPG.

The SPG, which is sometimes designated the pterygopalatine ganglion, is located in the pterygopalatine fossa of the human skull, close to the sphenopalatine foramen and close to the pterygoid canal. The SPG is situated below the maxillary nerve where the maxillary nerve crosses the pterygopalatine fossa. Although it is also connected functionally with the facial nerve, the SPG is intimately related with the maxillary division of the trigeminal nerve and its branches. The parasympathetic root of the SPG is formed by the nerve of the pterygoid canal, which enters the SPG posteriorly. The fibers of the parasympathetic root of the SPG are believed to arise from a special lacrimatory nucleus in the lower part of the pons and run in the sensory root of the facial nerve and its greater petrosal branch before the latter unites with the deep petrosal branch to form the nerve of the pterygoid canal. The sympathetic root of the SPG is also incorporated in the nerve of the pterygoid canal. The fibers of the sympathetic root of the SPG are postganglionic, arise in the superior cervical ganglion, and travel in the internal carotid plexus and the deep petrosal nerve. The vidian nerve is located in close proximity to the SPG, and the efficacy of local anesthetics for inhibiting an acute CNvD may arise, in whole or in part, from anesthesia of the vidian nerve or another DnNS located in close anatomic proximity to the SPG. It is also known that the trigeminal nerve has anatomical and functional relationship(s) to cervical nerve 2. Other DnNSs which are located in close anatomic proximity to the SPG include, but are not limited to, the cavernous sinus ganglion, the carotid sinus ganglion, numerous branches of the maxillary nerve, the ethmoidal nerve, and the ethmoidal ganglion.

The ability of a compound to diffuse from the surface of the nasal epithelium to a DnNS such as the SPG depends, of course, on the ability of the compound to diffuse through bodily tissues and fluids. Thus, compounds to be delivered to a DnNS by topical application to the nasal epithelium are preferably diffusible through both aqueous solutions and lipids.

Local anesthetics which are related to the class of local anesthetics designated aminoacyl local anesthetics exhibit both suitable aqueous solubility and suitable lipid solubility for use in the methods of the invention. It is believed that such local anesthetics are able to diffuse into nerves in their neutral, uncharged state, and that such local anesthetics assume their pharmacologically active, charged state within nerve cells.

In the case of delivery of a local anesthetic to a DnNS such as the SPG via topical application of the anesthetic to the nasal epithelium, it is preferable that the anesthetic be sufficiently diffusible through bodily tissues and fluids and have a sufficiently long half-life in vivo that the anesthetic is able to diffuse from the epithelium to the DnNS in an amount and for a duration sufficient to anesthetize the DnNS or otherwise inhibit the physiological processes that result in one or more symptoms of the CNvD, such as a period on the order of at least about one hour, and preferably at least about two hours. On the other hand, the diffusivity through bodily tissues and fluids and the in vivo half-life of the anesthetic must not be so high and long, respectively, that the anesthetic is delivered systemically in an amount sufficient to cause the adverse effects know s to be associated with systemic administration of local anesthetics (see, e.g., Physician's Desk Reference®, Medical Economics Co., Inc., Montvale, N.J., 51 st ed., 1997, pp. 424–427).

Apparatus for Intranasal or Dorsonasal Administration of a Composition

Particularly contemplated apparatus for intranasal or dorsonasal delivery of a composition to a human patient according to the methods of the invention include, but are not limited to, an anatomically-shaped applicator, a metered dose dispenser, a non-metered dose dispenser, a squeezable dispenser, a pump dispenser, a spray dispenser, a foam dispenser, a powder dispenser, an aerosol dispenser, a dispenser containing a propellant, an inhalation dispenser, a patch comprising the composition, an implant comprising the composition, a soft pipette with an elastomeric bulb in fluid communication with a reservoir containing the composition, a dropper for directing the composition past the conchae of the patient to a dorsonasal nerve structure, a swab having an absorbent portion impregnated with the composition, a swab having an anatomically-shaped portion comprising an absorbent portion impregnated with the composition, and a swab having a compressed absorbent portion in fluid communication with a reservoir containing the composition. An anatomically-shaped applicator is one which has a shape which permits insertion of the applicator into the nose or mouth of a human and which enables contact of the composition delivered by the applicator with the surface of the region of the nasal epithelium overlying the SPG or with a surface of the nasal epithelium near the region of the nasal epithelium overlying the SPG. It is preferred that the shape and/or materials of the apparatus be selected for comfortable insertion or application via an intranasal route.

Another embodiment of an apparatus for intranasal or dorsonasal delivery of a pharmaceutical composition of the invention comprises a body having a plurality of passages through which a composition may be delivered. The device may be designed so that the pharmaceutical composition of the invention is delivered through each passage, the passages being individually or collectively connected to, for example, a plurality of orifices in an anatomically-shaped applicator whereby the orifices direct delivery of the composition to a plurality of locations within the nasal cavity when the applicator is inserted into the nose of a patient and operated. The device may alternately be designed so that the pharmaceutical composition of the invention is delivered through one or more passages and an additional pharmaceutically active agent is delivered through the same passages or through one or more different passages. Alternately, the device may comprise components of the pharmaceutical composition of the invention which are separately delivered through one or more passages of the device and mixed either in a passage of the device or in the nasal cavity of the patient.

Devices which contain, deliver, or produce a semi-solid long-acting local anesthetic composition are contemplated. To use one of these devices, an outlet of the device is situated in fluid communication with one of or both of the nares of a patient. A solid, foam, semi-solid, foam-forming fluid, or another fluid which exhibits an increase in viscosity upon administration, such as one of the type known in the art, is provided to the outlet, whereby it passes into the nares of the patient, filling or partially filling the nasal cavity. A local anesthetic in the composition contacts the walls of the nasal cavity, preferably in a dorsonasal location, and the local anesthetic is thereby administered to the patient.

The Kit of the Invention

The invention additionally includes a kit comprising a long-acting local anesthetic pharmaceutical composition, as described herein, and an applicator, as also described herein, for intranasally, and preferably dorsonasally, administering the composition to a human patient to inhibit a CNvD. The kit is used by administering the composition to the patient at a time when the patient is experiencing a symptom of a CNvD episode or a prodromal symptom of a CNvD. The kit may further comprise a migraine therapeutic pharmaceutical agent, another pharmaceutically active agent, another local anesthetic, and the like. The kit may, and preferably does, further comprise instructional material which describes intranasal or dorsonasal administration of the composition to a patient. The instructional material may, for example, comprise written instructions to intranasally or dorsonasally administer the composition included in the kit in accordance with this invention.

The kit described herein may also be used for inhibition of muscular headaches. The components of the kit for this purpose are substantially the same, with the exception that any instructional material should describe the usefulness of the compositions and methods of the invention for inhibiting a muscular headache, rather than, or in addition to, a CNvD. If the kit may also be used to inhibit a muscular headache, in which instance the local anesthetic pharmaceutical composition need not be long-acting and is administered to the patient during a muscular headache episode.

Co-Administration of a Local Anesthetic and Another Compound to Effect Systemic Delivery of the Compound The invention further relates to the discovery that non-intravenous administration of a composition comprising a local anesthetic and a pharmaceutically active agent to an animal such as a mammal, particularly a human, improves systemic uptake of the agent in the animal, relative to the uptake achieved by non-intravenous administration of the agent alone to the animal by the same route.

The present invention includes a method of systemic drug delivery, the method comprising non-intravenously administering to a human patient a composition comprising a local anesthetic and a pharmaceutically active agent, whereby systemic delivery of the agent is improved relative to systemic delivery of the agent when delivered by the same non-intravenous route in the absence of the local anesthetic. The pharmaceutically active agent may be any drug. It is contemplated that this method of effecting systemic delivery is particularly useful for delivery of any agent which is able to diffuse through vascular and other tissues to a greater degree in the presence of the local anesthetic than in the absence of the local anesthetic. Thus, the agent may be, for example, a hormone, a peptide, a liposome, or a polymeric molecule such as heparin.

Any pharmaceutically active agent which is desired to be delivered systemically may be co-administered non-intravenously in a composition comprising the agent and a local anesthetic. Where the local anesthetic is not being administered for the purpose of inhibiting a CNvD, delivery of a composition comprising a local anesthetic and the agent intended for systemic delivery need not be directed to the dorsonasal region of the nasal cavity. Because the nasal cavity is highly vascularized, delivery of the composition may be directed to substantially any portion of the nasal epithelium to achieve systemic delivery of the agent. Furthermore, the composition may be delivered to any vascularized tissue, such as to the surface of a mucosal epithelium or to a skin surface, for example, to achieve systemic delivery of the agent.

The local anesthetic may be any local anesthetic except cocaine, which is a vasoconstrictor. The local anesthetic compounds, formulations, dosages, and methods of administration which are useful for this method of the invention are substantially the same as those described herein with respect to inhibiting a neurovascular headache, a muscular headache, or a CNvD. Compounds, formulations, and dosages of the other pharmaceutically active agents described in this method are known in the art. Owing, in part, to the vasodilatory activity of local anesthetics, these compounds may be used according to this method at doses of about half their art-recognized doses to their full art-recognized doses.
Theory Proposed to Explain the Mechanism of Improved Systemic Delivery of a Pharmaceutically Active Agent by Co-Administration with a Local Anesthetic Without wishing to be bound by any particular theory, it is believed that administration of a local anesthetic to a vascularized tissue induces dilation of blood vessels within the tissue. Vasodilation results in recruitment of surface blood vessels and increases the ability of a compound present in the tissue to pass into the systemic circulation. Therefore, co-administration to a tissue of a local anesthetic and a pharmaceutically active agent improves the ability of the agent to pass from the tissue to the bloodstream for systemic delivery.

Dosing Information Relevant to Systemic Drug Delivery

The local anesthetic doses and formulations which are useful for co-administration of the local anesthetic and another compound to effect systemic delivery of the compound are substantially the same as those described for the method of inhibiting a CNvD. In view of the present disclosure, it will be understood by the artisan of ordinary skill that the dose and formulation of the local anesthetic will depend upon, among other factors, the age, size, condition, and state of health of the animal, the anatomical location to which the composition will be delivered, the identity of the local anesthetic, and the identity of the compound to be co-administered. Substantially any amount of local anesthetic may be used. By way of example, compositions which comprise the compound to be co-administered and the local anesthetic at a concentration of about 0.01% to about 53% by weight, and preferably about 0.25% to about 10% by weight, more preferably about 0.5% to about 5% by weight, and most preferably about 2.5% by weight, may be used. The composition may be prepared as a liquid, a semi-solid, or a solid, as described herein. The composition may be formulated for intranasal, topical, subcutaneous, buccal, or substantially any other non-intravenous route of administration using methods and compositions well known in the art. The dose of the compound to be co-administered is dependent upon the identity of the compound, the purpose for which the compound is to be administered, and the size, age, condition, and state of health of the animal. Compounds, formulations, and dosages of pharmaceutically active agents described in this method are known in the art. Owing, in part, to the vasodilatory activity of local anesthetics, these compounds may be used according to this method at doses of about half their art-recognized doses to their full art-recognized doses.

While the invention has been described with reference to human anatomy, it is contemplated that the compositions and methods of the invention can be used analogously in any animal, particularly in any mammal, especially regarding co-adminstration of a local anesthetic and any pharmaceutically active agent to effect or enhance systemic delivery of the agent.

The invention is now described with reference to the following Examples. These Examples are provided for the purpose of illustration only and the invention should in no way be construed as being limited to these Examples, but rather, should be construed to encompass any and all variations which become evident as a result of the teaching provided herein.

EXAMPLE 1

Dorsonasal Administration of Ropivacaine for Inhibition of Acute Migraine Episodes The purpose of the experiments described in this Example was to determine the efficacy of dorsonasal administration of ropivacaine for inhibition of acute migraine episodes. Ropivacaine was dorsonasally administered to individual patients experiencing head pain, other symptoms, or both, believed to be associated with an acute migraine episode. Patients assessed head pain prior to and after ropivacaine administration.

Dorsonasally administered ropivacaine rapidly inhibited migraine in 92% of the ambulatory patients, as evidenced by an average 90% reduction in perceived pain within one hour, usually within 15 minutes or less. Symptoms of nausea and photophobia associated with acute migraine episodes in patients were similarly inhibited. Rebound of migraine occurred in only 5.4% of patients within twenty-four hours of treatment. These results demonstrate that dorsonasal administration of ropivacaine is an efficacious method of inhibiting an acute migraine episode.

The materials and methods used in the procedures performed in this Example are now described.
Ropivacaine Composition Ropivacaine-HCl (Naropin™, Astra USA, Westborough, Mass.) was used as the commercially-available 0.75% (w/v) solution, and was obtained in 30 milliliter, sterile injectable vials.
Methods of Ropivacaine Administration Three methods were used to achieve dorsonasal delivery of ropivacaine to individual patients. Ropivacaine was administered to a first group of patients by an intranasal drip method. Ropivacaine was administered to a second group using cotton swabs, the absorbent portions of which were saturated with the ropivacaine solution. Ropivacaine was administered to patients in a third group by spraying the ropivacaine solution into each nostril, using either a squeeze-type spray bottle or a metered-dose spray bottle.

The intranasal drip method used to administer ropivacaine to the first group of patients was a based on the method described by Barre (1982, Headache 22:69–73), except that the ropivacaine solution was used in place of the solution used by Barre. Approximately 0.75 milliliter to approximately 1.0 milliliter of the ropivacaine solution was administered by way of each of the nostrils of each patient.

The cotton swab method used to administer ropivacaine to the second group of patients comprised gently inserting cotton swabs, sequentially and bilaterally, into the nares of patients and urging the swabs dorsally until their absorbent portions contacted portions of nasal epithelium located dorsal to the middle conchae. Each swab was left in place for approximately one minute, and was then withdrawn. Approximately 0.5 milliliter of the ropivacaine solution was delivered to each nostril using this method.

Patients in a third group were administered ropivacaine by spraying less than about 0.5 milliliter of the ropivacaine solution into each of the patient's nostrils using either a sterile squeeze bottle or a sterile metered-dose spray bottle of known design. The design and operation of each of these spray bottles are well known in the art.

Prior to administration of ropivacaine, each patient was placed in a supine position with the patient's head hyperextended approximately 45 degrees and rotated approximately 30 degrees to the right side. In this position, an imaginary line extending from the region of the nasal epithelium overlying the SPG of the patient through the patient's left nostril was approximately vertical. Ropivacaine was then administered to the left nostril of the patient as described for each of the three groups of patients. Ropivacaine was administered to each patient's right nostril after rotating the patient's head approximately 30 degrees to the left. Ropivacaine was administered to both nostrils of each patient to prevent cases of unilateral migraine from developing into contralateral migraine.

Assessing Ropivacaine-Induced Pain Relief

Prior to ropivacaine administration, each patient rated perceived headache pain according to a standard pain scale of the type used in the art. Patients were asked to rank the severity of pain which they were experiencing on a scale from 0 (no pain) to 10 (worst pain imaginable). This ten-point pain rating scale is analogous to, but has more gradations than, the four-point rating system used by the International Headache Society (IHS; Headache Classification Committee of the International Headache Society, 1988, Cephalalgia 8(Suppl. 7):19–28). Ropivacaine was administered to one nostril of each patient, and then to the other. The time required to administer ropivacaine to both nostrils of each patient was approximately three minutes. Five minutes after the completion of administration of ropivacaine to the patient's first nostril, each patient again rated perceived headache pain. If no pain relief was evident, dosing was repeated, and the rating procedure was repeated. Pain ratings were obtained for each patient until peak effect appeared to be achieved, for up to ninety minutes, acutely. Follow-up of each patient's condition was attempted by direct contact or by telephone contact between six and eight hours post-treatment, between twenty-four and forty-eight hours post-treatment, and up to one week post-treatment.

The results obtained from the procedures performed in this Example are now described.

The population of patients treated in the procedures performed in this Example comprised forty-two adults, each of whom sought migraine relief. The results of treatment of each of these patients with either ropivacaine or (for three patients) lidocaine are presented in Table 1. The five patients who were either treated with lidocaine or did not clearly meet the IHS criteria for migraine were not included in the analysis presented herein of the efficacy of dorsonasal ropivacaine treatment of migraine. The demographic and pre-treatment characteristics of the patients who met IHS migraine criteria and who were treated with ropivacaine are presented in Table 2.

TABLE 1

Summary of Patient Data.

| Patient Identifier | Medical History[1] | Headache History[2] | Associated Symptoms[3] | Treatment[4] | Results[5] |
|---|---|---|---|---|---|
| P#1 | | Posterior Migraine | Mild Nausea Photophobia | R 0.75% 2 Sprays | Initial pain: 8 Pain 10 min post-treatment: 0 No rebound up to 24 hours |
| P#2 | Head Trauma Resulting From Auto Accident | Constant Headache for circa 28 years | | R 0.75% 2 cc Drops | No Relief[6] |
| P#3 | Meningitis circa 26 years pre-treatment | Monthly Headaches of circa 3 day duration | | R 0.75% 2 cc Drops | Transient Improvement[6] |
| P#4 | Post Partum Headaches | Migraine | | R 0.75% 2 cc Drops | Initial pain: 9 Pain 3 min post-treatment: 0 No rebound up to 24 hours |
| P#5 | | Posterior and Lateral Migraine | Nausea Photophobia | R 0.75% 2 cc Drops | Initial pain: 9 Pain 15 min post-treatment: 0 No rebound up to 24 hours |
| P#6 | Post Partum Headache | Temporal and Frontal Headache | | R 0.75% Sat'd Cotton Swab | Initial pain: 8 Pain 5 min post-treatment: 0 No rebound up to 24 hours |
| P#7 | | Temporal and Frontal Headache of 2–3 Day Duration | Visual Changes | R 0.75% Sat'd Cotton Swab | Initial pain: 10 Pain 2 min post-treatment: 0 No rebound up to 24 hours or up to 48 hours |
| P#8 | | Patient's First Vascular Headache Episode (CT scan ruled out sub-arachnoid hemorrhage) | Loss of Vision Bed-ridden | R 0.75% Sat'd Cotton Swab | Initial pain: 10 Pain 10 min post-treatment: 0 Pain 24 hours post-treatment: 1 (this pain was relieved by administering a 325 milligram Tylenol ™ (McNeil-PPC, Inc., Fort Washington, PA) tablet) No rebound up to two weeks |
| P#9 | | Migraine | | R 0.75% Sat'd Cotton Swab | Initial pain: 8.5 Pain 5 min post-treatment: 1 No rebound up to 3 days |
| P#10 | | Migraine | Nausea Photophobia | R 0.75% Sat'd Cotton Swab | Initial pain: 9 Pain 3 min post-treatment: 0 |

TABLE 1-continued

Summary of Patient Data.

| Patient Identifier | Medical History[1] | Headache History[2] | Associated Symptoms[3] | Treatment[4] | Results[5] |
|---|---|---|---|---|---|
| P#11 | | Occipital Headache few times per year | Must lie down | R 0.75% 2 cc Drops | Initial pain: 9 Pain 15 min post-treatment: 5 Pain 60 min post-treatment: 0 No rebound up to one week |
| P#12 | | Migraine | | L 2.0% 1 cc Drops | Initial pain: 7 Pain 5 min post-treatment: 2 Pain 45 min post-treatment: 6[B] |
| P#13 | Marfan's Syndrome | Migraine | Mild Nausea | R 0.75% 2 Sprays | Initial pain: 6 Pain 30 min post-treatment: 0[6] No rebound up to 24 hours |
| P#14 | | Migraine (Worst during menses) | Nausea Photophobia Visual changes | R 0.75% Sat'd Cotton Swab | Initial pain: 8 Pain 3 min post-treatment: 0 Pain 5 min post-treatment: 2 Pain 18 hrs post-treatment: 8 (After 18 hrs, treated w/spray) |
| | | | | Retreated with 2 Sprays | Pain following spray: 0[6] No rebound up to 48 hours |
| P#15 | Viral Gastro-intestinal Disturbance | Sinus Headache | Vertigo developed after sneeze | L 2.0% 1 cc Drops | Initial pain: 6 Pain 15 min post-treatment: 0 Pain 30 min post-treatment: 6 |
| P#16 | Post Partum Headache | Post Dural Puncture Headache | | L 2.0% 1 cc Drops | Initial pain: 8 Pain 15 min post-treatment: 4[6] |
| P#17 | | Migraine | Nausea Photophobia | R 0.75% 2 Sprays | Initial pain: 8 Pain 15 min post-treatment: 2 Pain 20 min post-treatment: 0[6] No rebound up to 48 hours |
| P#18 | | Migraine | Visual changes | R 0.75% Sat'd Cotton Swab | Initial pain: 9 Pain 3 min post-treatment: 0 |
| P#19 | Lumbar Disc Surgery | Migraine | | R 0.75% Sat'd Cotton Swab | Initial pain: 9 Pain 1 min post-treatment: 0 No rebound up to 48 hours |
| P#20 | Congenital Megacolon | Migraine | Nausea Vomiting | R 0.75% Sat'd Cotton Swab | Initial pain: 8 Pain 3 min post-treatment: 0 No rebound up to one week |
| P#21 | | Migraine | Nausea | R 0.75% Sat'd Cotton Swab | Initial pain: 10 Pain 3 min post-treatment: 1 Pain 5 min post-treatment: 0 No rebound up to one week |
| P#22 | | Cervical and Occipital Headache | | R 0.75% Sat'd Cotton Swab | Initial pain: 8 Pain 10 min post-treatment: 0 No rebound up to 24 hours |
| P#23 | Cervical Spine Pain | Cervical and Occipital Headache | Nausea | R 0.75% Sat'd Cotton Swab | Initial pain: 9 Pain 5 min post-treatment: 1 No rebound up to 24 hours |
| P#24 | | Migraine | | R 0.75% Sat'd Cotton Swab | Initial pain: 9 Pain 3 min post-treatment: 0 |
| P#25 | | Recurrent Parietal and Occipital Headaches, Bilateral Temporal Headaches | Nausea Visual changes | R 0.75% Sat'd Cotton Swab | Initial pain: 10 Pain 3 min post-treatment: 0 No rebound up to one week |
| P#26 | | Migraine | Nausea Photophobia | R 0.75% Sat'd Cotton Swab | Initial pain: 10 Pain 5 min post-treatment: 0 No rebound up to 24 hours |
| P#27 | | Recurrent Frontal, Parietal, | Nausea Photophobia | R 0.75% Sat'd Cotton | Initial pain: 10 Pain 8 min |

TABLE 1-continued

Summary of Patient Data.

| Patient Identifier | Medical History[1] | Headache History[2] | Associated Symptoms[3] | Treatment[4] | Results[5] |
|---|---|---|---|---|---|
| | | Temporal, and Occipital Headaches | | Swab | post-treatment: 0 No rebound up to 48 hours |
| P#28 | | Migraine | Nausea Visual changes | R 0.75% Sat'd Cotton Swab | Initial pain: 9 Pain 5 min post-treatment: 0 No rebound up to 48 hours |
| P#29 | | Migraine | Nausea Photophobia | R 0.75% Sat'd Cotton Swab | Initial pain: 10 Pain 5 min post-treatment: 0 No rebound up to 24 hours |
| P#30 | Temporal Arteritis, Steroid Use | Migraine | Nausea | R 0.75% Sat'd Cotton Swab | Initial pain: 9 Pain 10 min post-treatment: 1 No rebound up to 18 hours |
| P#31 | | Migraine | | R 0.75% Sat'd Cotton Swab | Initial pain: 9 Pain 2 min post-treatment: 1 No rebound up to 24 hours |
| P#32 | Chemotherapy | Migraine | Nausea | R 0.75% Sat'd Cotton Swab | Initial pain: 10 Pain 15 min post-treatment: 0 |
| P#33 | Hypertension, Controlled Diet | Migraine | Nausea, Photophobia, Visual changes | R 0.75% 2 Metered Sprays | Initial pain: 9 Pain 5 min post-treatment: 5 Pain 30 min post-treatment: 3 Pain 90 min post-treatment: 0 (Patient presented one week later) |
| | | Migraine | | 2 Metered Sprays | Initial pain: 10 Pain 15 min post-treatment: 5 Pain 30 min post-treatment: 4 Pain 90 min post-treatment: 0 No rebound up to one week |
| P#34 | Major Depression, Chronic Hepatitis C | Migraine | Nausea, Photophobia | R 0.75% 2 Metered Sprays | Initial pain: 7 Pain 20 min post-treatment: 3 (Then repeated treatment using two metered sprays) |
| | | | | 2 Metered Sprays | Pain 5 min post-treatment: 0 (Patient presented seven hours later) |
| | | | | 2 Metered Sprays | Initial pain: 2 Pain 10 min post-treatment: 0 No rebound up to 24 hours |
| P#35 | Head Trauma | Migraine | Nausea, Visual changes | R 0.75% 2 Metered Sprays | Initial pain: 8 Pain 30 min post-treatment: 6 Pain 60 min post-treatment: 2 |
| P#36 | Complaints of "Stuffy Nose" | Migraine | Nausea, Photophobia, Visual changes | R 0.75% 2 Metered Sprays | Initial pain: 9 Pain 5 min post-treatment: 7 Pain 30 min post-treatment: 5 |
| P#37 | | Atypical Right Side Headache Behind Eye | Nausea, Photophobia, Intense Eye Pain & Pressure | R 0.75% 2 Metered Sprays | Initial pain: 7 Pain 30 min post-treatment: 3 Pain 45 min post-treatment: 0 (Patient presented three days later) |
| | | | | 2 Metered Sprays | Initial pain: 2 Pain 10 min post-treatment: 0 No rebound up to 48 hours |
| P#38 | Head Trauma | Migraine | | R 0.75% 2 Metered Sprays | Initial pain: 3 Pain 30 min post-treatment: 0 |
| P#39 | | Migraine | Nausea | R 0.75% 2 Sprays | Initial pain: 9 Pain 2 min post-treatment: 0 No rebound up to 48 hours |

TABLE 1-continued

Summary of Patient Data.

| Patient Identifier | Medical History[1] | Headache History[2] | Associated Symptoms[3] | Treatment[4] | Results[5] |
|---|---|---|---|---|---|
| P#40 | | Migraine | Mild Nausea | R 0.75% Sat'd Cotton Swab | Initial pain: 10 Patient exhibited apparent allergic reaction between 5 and 15 minutes post-treatment Pain 20 min post-treatment: 3 Pain 30 min post-treatment: 5 Level 5 pain endured 8 hours |
| P#41 | Head Trauma | Recurrent Headaches | Nausea, Photophobia, Perceived 'Whistling Sounds' | R 0.75% Sat'd Cotton Swab | Initial pain: 8 Pain 20 min post-treatment: 0 No rebound up to 48 hours |
| P#42 | | Migraine | Perceived 'Flashing Lights' | R 0.75% Sat'd Cotton Swab | Initial pain: 9 Pain 2 min post-treatment: 0 No rebound up to one week |

Notes:
[1]"Medical History" refers to events in the patient's medical history deemed potentially related to the patient's headache symptoms.
[2]"Headache History" describes the headache for which treatment was sought by the patient.
[3]"Associated Symptoms" describes symptoms described by the patient as accompanying the headache for which treatment was sought, past recurrent headache episodes, or both.
[4]"Treatment" indicates the compound which was administered to the patient: "R" refers to ropivacaine; "L" refers to lidocaine; #% refers to the concentration of the solution comprising the compound (expressed as % w/v); "2 Sprays" refers to delivery of less than about 0.5 milliliter of the indicated solution delivered by two sprays into each nostril of the patient using a sterile squeeze bottle containing the solution; "# cc Drops" refers to the delivery of # milliliters of the indicated solution via the modified nasal drip method described herein; "Sat'd Cotton Swab" refers to delivery of the indicated solution using a standard cotton swab saturated with the indicated solution as described herein; "2 Metered Sprays" refers to delivery of less than about 0.5 milliliter of the indicated solution delivered by a combination of two sprays into each nostril of the patient using a sterile metered-dose spray bottle containing the solution.
[5]"Results" refers to pain relief experienced by each patient, using the pain rating method of the International Headache Society (i.e. 10 = worst pain imaginable; 0 = no pain). The term "min" means minutes.
[6]This patient experienced oropharyngeal numbness.

TABLE 2

Demographic and Pretreatment Characteristics of Patients.

| Characteristic | Value |
|---|---|
| Mean Age (Standard Error; Range) | 45.1 years (±2.1 years; 22–67) |
| Gender | |
| Male | 17 (45.9%) |
| Female | 20 (54.1%) |
| Duration of Current Headache, hours (Standard Error) | 23.2 (±4.1) |
| Mean Pain Level on 10-Point Scale (Standard Error; 95% conf. interval) | 8.64 (±0.223; 8.18–9.09) |
| Patients Experiencing Nausea | 23 (62.1%) |
| Patients Experiencing Photophobia | 14 (37.8%) |

Thirty-four of the thirty-seven (92%) migraine patients treated with ropivacaine experienced significant (i.e. certainly greater than 50%) reduction of migraine severity. Complete relief followed ropivacaine administration in 72% of the patients. Photophobia, nausea, and pain were simultaneously eliminated in migraine patients who experienced each of these symptoms. Rebound was evident in only two of the responding patients, meaning that the rebound rate was only 5.4%. Adverse effects of ropivacaine administration were minimal: one patient experienced an allergic response to ropivacaine administration, which response consisted of short-lived tachycardia, dizziness, and wheezing, all of which endured for about twenty minutes before subsiding. Even this patient who experienced an allergic response experienced a measurable reduction of migraine pain within twenty-five minutes post-treatment.

Pain Relief Effected by Cotton-Swab-Application of Ropivacaine

Among the twenty-four patients to whom ropivacaine was dorsonasally administered using a cotton swab, the mean pain severity rating prior to administration of ropivacaine was 9.06±0.16 points out of a possible 10 points (mean±standard error). The mean post-administration pain severity rating at the time of peak effect was 0.33±0.14 points out of a possible 10 points. Thus, dorsonasal administration of ropivacaine using a cotton swab resulted in a mean peak headache severity rating reduction of 8.73±0.249 points. The mean time that elapsed between the time of treatment and the perception by the patient of the peak effect was 7.41±1.47 minutes. Every patient in this group responded to treatment, 95% of the patients achieving a pain severity rating of zero or one, and 72% of patients achieving a pain severity rating of zero. One patient in this group experienced rebound of headache pain eighteen hours post-treatment. Thus, dorsonasal administration of ropivacaine using a cotton swab causes significant pain reduction in 100% of migraine patients, with rebound occurring in only 4% of patients.

Pain Relief Effected by Nasal-Drip-Application of Ropivacaine

Dorsonasal administration of ropivacaine effected by delivery of nasal drops resulted in a mean peak headache severity rating reduction of 9.00 points out of a possible 10 points in the three patients so treated. The mean time that elapsed between the time of treatment and the perception by the patient of the peak effect was 26.00±17.37 minutes. None of the three patients experienced migraine rebound.

Pain Relief Effected by Nasal-Spray-Application of Ropivacaine

Dorsonasal administration of ropivacaine effected by delivery using the nasal spray method resulted in a mean peak headache severity rating reduction of 6.22±0.66 points out of a possible 10 points in the ten patients so treated. The mean time that elapsed between the time of treatment and the perception by the patient of the peak effect was 33.9±8.48 minutes. Of the ten migraine patients treated by intranasal spray, all experienced significant reduction in headache pain severity. The majority of these patients experienced complete headache pain relief and did not experience rebound. The remainder experienced a mean headache pain severity rating reduction of 87.5±6.49%. One of the ten patients to whom ropivacaine was administered using a spray bottle experienced a separate episode of migraine one week later.

Comparison of Administration of Ropivacaine by Cotton Swab, by Nasal Drops, and by Nasal Spray The results obtained in patients who were administered ropivacaine by the three methods described herein are summarized in Tables 3 and 4.

TABLE 3

Effect of the Route of Ropivacaine Administration on Severity of Migraine Pain. Pain Ratings and Pain Relief are measured using a 10-point pain scale, as described herein.

| Method of Delivery | Pain Rating Prior to Administration | Pain Rating After Administration | Pain Relief |
|---|---|---|---|
| Cotton Swab | 9.06 | 0.33 | 8.73 |
| Nasal Drops | 9.00 | 0.00 | 9.00 |
| Nasal Spray | 7.22 | 1.00 | 6.22 |

TABLE 4

Effect of the Route of Ropivacaine Administration on Severity of Migraine Pain.

| Method of Delivery | Number of Patients | Mean Reduction in Pain Rating (IHS points) | Mean Time Until Maximal Effect | Rate of Pain Relief (IHS points per minute) |
|---|---|---|---|---|
| Cotton Swab (Standard Error) 95% confid. interval | 24 | 8.64 (±0.25) 8.12–9.16 | 7.41 (±1.46) 4.37–10.4 | 2.32 |
| Nasal Drops (Standard Error) 95% confid. interval | 3 | 9.00 (0) 5.89–10.6 | 26.0 (±12.3) 0–100 | 1.25 |
| Nasal Spray (Standard Error) 95% confid. interval | 10 | 6.22 (±0.66) 4.69–7.75 | 33.9 (±8.48) 14.31–53.46 | 0.287 |

Comparison of the Therapeutic Effect of Dorsonasally-Administered Ropivacaine and the Therapeutic Effect of Intranasally-Administered Lidocaine The anesthetic effect of 0.75% (w/v) ropivacaine-HCl is approximately equivalent to that of 3% (w/v) lidocaine. Intranasal spray administration of 1–2 milliliters of a 4% (w/v) lidocaine solution was 55% effective to reduce pain associated with migraine (Maizels et al., 1996, J. Amer. Med. Assoc. 276:319–321). By comparison, as described herein, dorsonasal spray administration of a 0.75% (w/v) ropivacaine solution was 100% effective to reduce pain associated with migraine. Furthermore, when dorsonasal administration of the ropivacaine solution was effected by topical application using a cotton swab saturated with the solution, reduction of migraine pain was achieved in 100% of patients. Preliminary data indicate that bupivacaine exhibits efficacy similar to that of ropivacaine for the relief of headache pain associated with migraine.

A comparison of ropivacaine and lidocaine on the basis of migraine pain relief per unit weight is provided in Table 5.

This comparison indicates that dorsonasally spray-administered ropivacaine is 2.4 times as potent as intranasally spray-administered lidocaine, and that dorsonasally swab-administered ropivacaine is more than 15 times as potent as intranasally spray-administered lidocaine. Furthermore, as indicated in Table 5, the rate of migraine rebound is much lower following dorsonasal administration of ropivacaine, whether administered by nasal spray or by cotton swab, than it is following intranasal administration of lidocaine. Thus, the data presented herein indicate that ropivacaine is a much more efficacious agent for migraine pain relief than is lidocaine and that treatment of migraine by dorsonasal ropivacaine administration has a significantly lower rebound rate than treatment by intranasal administration of lidocaine.

TABLE 5

Comparison of the efficacy of migraine treatment by dorsonasal ropivacaine administration and the efficacy by intranasal lidocaine administration. "Rate" indicates the rate of migraine pain reduction per minute per gram of drug administered to the patient. Pain was rated using a 10-point pain scale, as described herein.

| Drug | Route of Administration | Rate of Pain Relief | Relative Efficacy[1] | Rebound Rate |
|---|---|---|---|---|
| Lidocaine | Intranasal Spray | 10.0 | 1.00 | 42% |
| Ropivacaine | Dorsonasal Spray | 24.5 | 2.45 | 10% |
| Ropivacaine | Dorsonasal Swab | 155 | 15.5 | 4% |

[1]Relative Efficacy means the Rate of Pain Relief for the indicated drug administered by the indicate route divided by the Rate of Pain Relief for intranasally spray-administered lidocaine.

Figure 3:
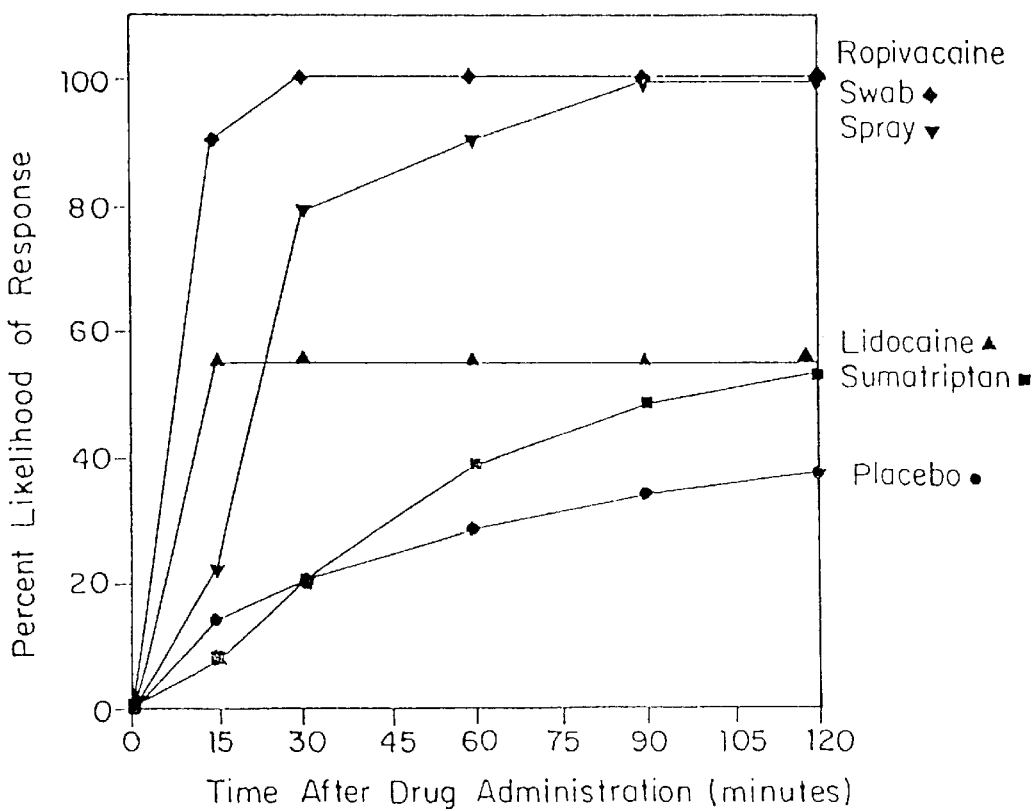
FIG. 3 is a graph which depicts the percentage of patients who exhibited at least 50% reduction in pain intensity following administration of various pharmaceutically active agents. The response of patients to whom a placebo was a placebo is indicated by filled circles (●; data from Maizels et al., 1996, J. Amer. Med. Assoc. 276:319–321 and The Subcutaneous Sumatriptan International Study Group, 1991, New Eng. J. Med. 325:316–321); the response of patients to whom sumatriptan was administered (as described in The Subcutaneous Sumatriptan International Study Group, 1991, New Eng. J. Med. 325:316–321) is indicated by filled squares (■); the response of patients to whom lidocaine was administered (as described in Maizels et al., 1996, J. Amer. Med. Assoc. 276:319–321) is indicated by filled triangles (▲); the response of patients to whom ropivacaine was administered by nasal spray as described herein in Example 1 is indicated by filled inverted triangles (▼); the response of patients to whom ropivacaine was administered by cotton swab as described herein in Example 1 is indicated by filled diamonds (♦).

Comparison of the Therapeutic Effect of Ropivacaine and the Therapeutic Effects of Other Anti-Migraine Pharmaceutically Active Agents In FIG. 3, the data obtained from the procedures performed in this Example are presented and compared with recently reported data obtained for administration of lidocaine to migraine patients (Maizels et al., 1996, J. Amer. Med. Assoc. 276:319–321) or administration of sumatriptan to migraine patients (The Subcutaneous Sumatriptan International Study Group, 1991, New Eng. J. Med. 325:316–321). Administration of ropivacaine resulted in an earlier onset of relief and a higher response rate than did administration of sumatriptan. Although the time of onset of relief using ropivacaine was roughly equal to the time of onset of relief using lidocaine, administration of ropivacaine treatment resulted in a nearly two-fold greater response rate than did administration of lidocaine. The response rate obtained by administration of ropivacaine to migraine patients was greater than the response rate obtained by administration of rizatriptan to such patients. In addition, the rebound rate following ropivacaine administration was lower than the rebound rate following rizatriptan administration (Kramer et al., 1997, Headache 36:268–269). The rapid and non-relapsing effects attributable to dorsonasal administration of ropivacaine are not observed following administration of lidocaine or a serotonin receptor agonist administered by the same route (Mills et al., 1997, Ann. Pharmacother. 31:914–915; Moore et al., 1997, Cephalalgia 17:541–550; Kramer et al., 1997, Headache 36:268–269).

While not wishing to be bound by any particular theory of operation, it is believed that dorsonasally administered ropivacaine inhibited migraine by anesthetizing a DnNS such as the SPG. Ropivacaine is ideally suited for anesthesia of a DnNS in general, and for migraine relief in particular. Ropivacaine exhibits intermediate lipid solubility and an intermediate half life in vivo, properties that limit possible toxicity. Direct application of ropivacaine to the region of the nasal epithelium overlying the SPG reduces the likelihood of systemic distribution of the compound, thereby limiting the likelihood of numerous side effects. Furthermore, direct application of ropivacaine to the region of the nasal epithelium overlying the SPG reduces the amount of ropivacaine which must be administered in order to provide an effective concentration at the SPG for relief of an acute migraine episode. Ropivacaine and other local anesthetics related to aminoacyl local anesthetics are known to selectively affect sensory neurons, relative to motor neurons, representing another advantage of using ropivacaine in the method of the invention. It is believed that direct administration of ropivacaine to the region of the nasal epithelium overlying the SPG, or to the region of the nasal epithelium near that region, arrests the cascade of neurotransmitter and neuropeptide release and stimulation that lead to neurogenic inflammation observed in the course of an acute migraine episode.

The ropivacaine molecule has the following structure (III), wherein the carbon atom indicated by the asterisk is a chiral center:

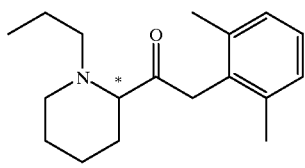

(III)

Cardiotoxicity is a side effect of administration of the R(dextro) enantiomer of ropivacaine, but this side effect is not exhibited by the S(levo) enantiomer (deJong, 1995, Reg. Anesth. 20:474–481). For this reason, ropivacaine is prepared as a sterile solution containing only the S(levo) enantiomer. The bupivacaine molecule also comprises a chiral center, but currently commercially available bupivacaine preparations include both the S and the R enantiomers.

Many of the patients described in this Example were observed for up to seven days, and 95% of those patients experienced no rebound during this period. This result contrasts with the results obtained following intranasal lidocaine administration. Of the 55% of patients who exhibited relief following intranasal lidocaine administration, at least 42% experienced rebound, usually within one hour post-treatment (Maizels et al., 1996, J. Amer. Med. Assoc. 276:319–321). Similarly, administration of either sumatriptan or rizatriptan resulted in inhibition of pain in 40–50% of patients within two hours post treatment, and patients who were administered either of these compounds frequently experienced rebound (The Subcutaneous Sumatriptan International Study Group, 1991, New Eng. J. Med. 325:316–321; Kramer et al., 1997, Headache 36:268–269).

EXAMPLE 2

Dorsonasal Administration of Bupivacaine for Inhibition of Acute Migraine Episodes The purpose of the experiments described in this Example was to determine the efficacy of dorsonasal administration of bupivacaine for inhibition of acute migraine episodes. Bupivacaine was dorsonasally administered to individual patients experiencing head pain, other symptoms, or both, believed to be associated with an acute migraine episode. Patients assessed head pain prior to and after bupivacaine administration.

Dorsonasally administered bupivacaine provided rapid arrest of migraine in all seven patients to whom it was administered within 10 minutes or less. Symptoms such as nausea, visual changes, and photophobia associated with acute migraine episodes in the patients were similarly reduced. Six of the seven patients treated using bupivacaine experienced no rebound of their migraine within twenty-four hours of treatment. The other patient experienced a recurrence of head pain four hours following a first administration of bupivacaine and another episode of head pain eight hours following a second administration of bupivacaine. These results demonstrate that dorsonasal administration of bupivacaine is an efficacious method of inhibiting an acute migraine episode.

The materials and methods used in the procedures performed in this Example were substantially the same as the materials and methods described in Example 1, with the exception that the composition which was administered to the patients described in this example comprised a 0.75% (w/v) solution of bupivacaine.

The results of treatment of each of the seven patients described in this Example with bupivacaine are presented in Table 6. The organization of and the abbreviations used in Table 6 are analogous to those used in Table 1, with the exception that "B" in the treatment column refers to bupivacaine. These results indicate that dorsonasal administration of bupivacaine is effective to inhibit acute migraine episodes.

TABLE 6

Summary of Patient Data.

| Patient Identifier | Medical History | Headache History | Associated Symptoms | Treatment | Results |
|---|---|---|---|---|---|
| P2#1 | | Migraine | Nausea | B 0.75% 2 Sprays | Initial pain: 5 Pain 10 min post-treatment: 0 No rebound up to 24 hours |
| P2#2 | | Migraine | Nausea Photophobia | B 0.75% Sat'd Cotton Swab | Initial pain: 7 Pain 5 min post-treatment: 0 No rebound up to 24 hours |
| P2#3 | | Migraine | Visual Changes and nausea as aura. Followed by head pressure and severe head pain at right occipital to front areas | B 0.75% 2 cc Drops | Initial pain: 10 Pain 5 min post-treatment: 1–2 Head pressure persisted No rebound up to 24 hours |
| P2#4 | Sinus Surgery | Migraine Triggered by Chocolate Ingestion | | B 0.75% 2 Sprays | Initial pain: 8 Pain 5 min post-treatment: 0 Recurrence 4 hours post-treatmt. Pain 5 min |

TABLE 6-continued

Summary of Patient Data.

| Patient Identifier | Medical History | Headache History | Associated Symptoms | Treatment | Results |
|---|---|---|---|---|---|
| | | | | | post-2nd-treatment: 0 Recurrence 8 hours post-treatmt. |
| P2#5 | | Mixed Headache | Nausea Photophobia | B 0.75% 2 Sprays | Initial pain: 8 Pain 10 min post-treatment: 0 No rebound up to 24 hours |
| P2#6 | | Migraine | | B 0.75% 2 Sprays | Initial pain: 8 Pain 3 min post-treatment: 0 No rebound up to 24 hours |
| P2#7 | | Migraine | Visual Changes | B 0.75% 2 cc Drops | Initial pain: 10 Pain 10 min post-treatment: 0 No rebound up to 24 hours |

EXAMPLE 3

Inhibiting a Recurring Cerebral Neurovascular Disorder by Dorsonasally Administering a Long-acting Local Anesthetic Decreases the Frequency and Severity of Subsequent Episodes The following studies relate to the methods of decreasing the frequency and severity of CNvD episodes described herein, and involved three patients.

A 25-year-old female patient, herein designated "patient 3-1" was afflicted with recurring severe migraine, wherein acute migraine episodes were associated with nausea and visual changes. Patient 3-1 generally rated the severity of head pain associated with acute migraine episodes in the range from five to eight using the pain scale described herein. Patient 3-1 experienced, on average, about one acute migraine episode per week prior to beginning dorsonasal ropivacaine therapy. In addition, patient 3-1 also usually experienced about one severe acute migraine episode per month, associated with menses, wherein the severity of head pain was from eight to ten using the pain scale described herein. Patient 3-1 did not respond satisfactorily to administration of beta blockers and sumatriptan.

Ropivacaine was dorsonasally administered to patient 3-1 using the cotton swab technique described herein. The patient has consistently experienced relief from all of the symptoms of her CNvD episodes within 3 to 5 minutes following administration of ropivacaine, regardless of whether the episodes are associated with menses.

Patient 3-1 has continued treatment according to this method for about six months. After beginning the ropivacaine treatment, the patient discontinued use of sumatriptan and propanolol. Discontinuing, these medications did not result in a loss of efficacy attributable to ropivacaine administration. Starting about three or four months following initiation of ropivacaine administration, the patient noticed a decrease in the initial severity of acute migraine episodes not associated with menses. At about the same time, the patient further noticed a decrease in the frequency with which acute migraine episodes not associated with menses occurred. No decrease in either the initial severity or the frequency of acute migraine episodes associated with menses has been reported by the patient. Patient 3-1 continues to experience relief from the head pain and other symptoms of acute migraine episodes, including those associated with menses, upon administration of ropivacaine.

A 45-year-old male, herein designated, "patient 3-2," was afflicted with recurring migraines. The acute migraine episodes began when he was a teenager, and have significantly worsened over the past 15 years. Head pain associated with the patient's acute migraine episodes is typically preceded by visual changes which he describes as a curtain-like wave of scotomata moving from left to right until he is unable to see. The patient then becomes disoriented with respect to time and place and must sit or lay down. Following these prodromal symptoms, a severe headache, rated 10 on the pain scale described herein, begins and typically endures for 45 to 60 minutes. The patient remains completely debilitated for the duration of the headache, unable to move about or walk. As the headache subsides, the patient's vision returns, and the patient is left feeling exhausted, as if he had not slept the night before.

Following dorsonasal administration of ropivacaine, delivered by the nasal spray method described herein, patient 3-2 noticed an abrupt halt to the progression of visual changes and steady resolution of his visual deficit. The headache rapidly decreased in intensity, decreasing from a pain intensity of 10, using the pain scale described herein, to an intensity of 2-3 within one to two minutes. The headache was completely resolved by fifteen minutes following ropivacaine administration. This patient also noted that he did not feel exhausted following the treated acute migraine episode. After four to six months of dorsonasal ropivacaine therapy, the patient noted that his headaches occurred less frequently, at a rate of approximately one headache every two months or longer. Furthermore, the severity of the headaches that patient 3-2 experienced was significantly reduced following this course of therapy. Prior to the course of dorsonasal ropivacaine therapy, the patient's headaches ordinarily had a pain intensity of about 10; after four to six months of this therapy, the initial headache pain (i.e. even prior to ropivacaine administration) was not greater than about 2. The patient reports significant lifestyle improvement, and is not aware of any other changes, for example changes in diet, sleep, exercise, environment, or medication, that could account for this improvement.

A 40-year-old female, herein designated, "patient 3-3," experienced about 3 to 5 recurring migraine episodes per week prior to beginning dorsonasal ropivacaine therapy. The initial severity of these headaches was reported to be 10, using the pain scale described herein. When ropivacaine was administered, using the saturated swab method described herein, to patient 3-3 during a headache episode, the patient reported a decrease in head pain from a rating of 10 to a rating of 0 or 1 within 10 minutes following ropivacaine administration. Furthermore, after three months of dorsonasal ropivacaine treatment, patient 3-3 reported that the frequency of her headache episodes had decreased to about 1 to 2 times weekly and that the initial severity of her headaches was in the range from about 7 to about 8, rather than 10.

The data described in this Example indicate that dorsonasal administration of ropivacaine to a patient afflicted with a recurring CNvD both inhibits a single episode of the CNvD and decreases the frequency and initial severity of the episodes associated with the recurring CNvD. Thus, the compositions, kits, and methods of the invention are useful for decreasing the frequency with which a patient afflicted with a recurring CNvD experiences a CNvD episode and for otherwise inhibiting the CNvD.

EXAMPLE 4

Inhibition of Tinnitus by Dorsonasal Administration of Ropivacaine

The data presented in this example demonstrate that symptoms of tinnitus may be inhibited by dorsonasal administration of a local anesthetic. Ropivacaine was dorsonasally administered to each of three patients using the nasal spray method or the nasal drops method described herein. All three patients experienced inhibition of tinnitus.

The first patient, herein designated, "patient 4-1," was a healthy male patient in his thirties who was afflicted with occasional migraines complicated by bilateral tinnitus about once every two to three months. Dorsonasal spray administration of ropivacaine to patient 4-1 relieved the head pain and tinnitus symptoms experienced by this patient within about five minutes following administration.

The second patient, herein designated, "patient 4-2," was a male in his forties who was afflicted with chronic head, neck, back, and shoulder pain resulting from trauma sustained during multiple motor vehicle accidents. Patient 4-2 was afflicted with constant head pain for which he used large quantities of intranasally-administered butorphanol. It was believed that the patient's headaches did not have a neurovascular etiology. Patient 4-2 is also afflicted with continuous bilateral tinnitus. Following dorsonasal spray administration of ropivacaine to patient 4-2, the patient reported a decrease in head pain of about 2 points, using the pain scale described herein, and furthermore experienced complete relief from symptoms of tinnitus for a period of 30 to 45 minutes. Interestingly, this patient noted a faster onset and a far more powerful effect on his chronic non-headache pain of intranasally administered butorphanol following intranasal administration of ropivacaine.

The third patient, herein designated, "patient 4-3," was a healthy male in his sixties who was afflicted with bilateral tinnitus for over 30 years. Following dorsonasal administration of 1 milliliter of 0.75% (w/v) ropivacaine into each nostril by the nasal drop method described herein, patient 4-3 experienced complete relief from tinnitus symptoms in his left ear and a 50–75% reduction in tinnitus symptoms in his right ear. This patient's relief from and reduction of symptoms persisted for about 30 to 45 minutes, after which period the tinnitus symptoms returned.

The results of the experiments described in this Example indicate that dorsonasal administration of a local anesthetic inhibits tinnitus. Even though the relief of tinnitus in these three patients was relatively short-lived (relative to migraine relief, as described herein), it must be borne in mind that no effective treatment exists for tinnitus. Thus, the treatment method described herein for tinnitus can be used to provide at least temporary relief to patients who have no effective long-term treatment options. Furthermore, the results presented in this Example suggest that a sustained release preparation of a local anesthetic or a local anesthetic causing a longer duration of anesthesia than ropivacaine may provide a longer period of inhibition of tinnitus than the ropivacaine preparation used in this method.

EXAMPLE 5

Dorsonasal Administration of Bupivacaine for Treatment of Muscular Headache Episodes The purpose of the experiments described in this Example was to determine the efficacy of dorsonasal administration of bupivacaine for inhibition of muscular headaches. Bupivacaine was dorsonasally administered to four individual patients experiencing head pain and other symptoms associated with a severe muscular headache episode. All of the patients had areas of sustained craniocervical muscle contraction and tenderness which was absent in all patients following headache resolution. Patients assessed head pain prior to and after bupivacaine administration. The four patients and their responses were as follows.

Patient 1

This patient was a 68-year-old female who experienced classic tension headache symptoms under stress. The patient normally experienced relief of tension headache symptoms following administration of ibuprofen. The patient was administered 0.75% bupivacaine during a tension headache episode, and thereafter experienced relief of her headache symptoms. The patient's pain intensity, as assessed using the pain scale described herein, decreased from about 8 to 0 within about 15 minutes after bupivacaine administration.

Patient 2

This patient was a 38-year-old male who experienced typical muscle contraction headache symptoms. The patient normally experienced relief of headache symptoms following administration of acetaminophen. The patient was administered 0.75% bupivacaine during a muscle contraction headache episode, and thereafter experienced relief of his headache symptoms within seven minutes following bupivacaine administration. The patient's pain intensity, as assessed using the pain scale described herein, decreased from about 7 to 0 within about 7 minutes after bupivacaine administration.

Patient 3

This patient was a 25-year-old male who experienced cervical neck pain symptoms associated with tension headache. The patient experienced moderate relief of headache symptoms following administration of non-steroidal anti-inflammatory drugs, including ibuprofen. The patient was administered 0.75% bupivacaine during a tension headache episode, and thereafter experienced relief of his headache symptoms. The patient's pain intensity, as assessed using the pain scale described herein, decreased from about 5 to about 1 within about 5 minutes after bupivacaine administration.

Patient 4

This patient was a 44-year-old female who experienced tension headaches. The patient was administered 0.75% bupivacaine during a tension headache episode, and thereafter experienced relief of neck pain and bi-temporal tension headache pain symptoms. The patient's pain intensity, as assessed using the pain scale described herein, decreased from about 7 to about 1 within about 5 minutes after bupivacaine administration. Prior to bupivacaine administration, the patient experienced mild residual pain in response to deep palpation of affected neck and temple muscles. This pain was perceived to be markedly decreased following treatment, and muscle knots were no longer perceived 5 minutes after treatment.

It is recognized that the muscular headache inhibition described in this Example may have been secondary to neurovascular effects of a dorsonasally administered local anesthetic or to effects on one or both of intracranial or extracranial neural or vascular structures, as described herein.

EXAMPLE 6

Dorsonasal Administration of a Eutectic Mixture of Local Anesthetics

An amount (0.5–1.0 milliliters) of a commercially available eutectic mixture of local anesthetics (prilocaine/lidocaine, 2.5% (w/v) each; Emla™, Astra USA, Westborough, Mass.) was dorsonasally administered to each of six healthy adults using a syringe having a flexible applicator attached thereto. None of the six adults noted oropharyngeal numbness, unpleasant taste, or any other side effect normally associated with administration of a local anesthetic following intranasal administration.

The same amount of the mixture was dorsonasally administered to five patients afflicted with headaches. Each of these five patients experienced complete or nearly complete inhibition of head pain and other symptoms of their headaches within ten minutes following administration.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting a cerebral neurovascular disorder in a human patient, the method comprising dorsonasally administering to the patient over a period of time of less than about one half hour a composition comprising a long-acting local anesthetic other than 2-(diethylamino)-N-(2, 6dimethylphenyl)acetamide or cocaine in an amount effective to anesthetize a dorsonasal nerve structure, whereby anesthetizing the dorsonasal nerve structure is effective, following completion of the administration of the composition, to inhibit the cerebral neurovascular disorder for greater than one hour.

2. The method of claim 1, wherein the cerebral neurovascular disorder is selected from the group consisting of tinnitus, cerebrovascular spasm, seizure, a disorder manifested during or after and associated with an acute ischemic event, and a neurovascular headache.

3. The method of claim 2, wherein the cerebral neurovascular disorder is a neurovascular headache.

4. The method of claim 3, wherein the neurovascular headache is selected from the group consisting of a migraine, a cluster headache, and a headache associated with a vascular disease.

5. The method of claim 4, wherein the neurovascular headache is a migraine.

6. The method of claim 1, wherein the cerebral neurovascular disorder is an acute cerebral neurovascular disorder.

7. The method of claim 6, wherein the acute cerebral neurovascular disorder is selected from the group consisting of a tinnitus episode, an individual seizure, an episode of cerebrovascular spasm, an acute migraine episode, an individual headache episode associated with a cluster headache, and an individual headache associated with a vascular disease.

8. The method of claim 7, wherein the acute cerebral neurovascular disorder is an acute migraine episode.

9. The method of claim 1, wherein the composition comprising the long-acting local anesthetic other than lidocaine or cocaine comprises at least one local anesthetic ingredient selected from the group consisting of a long-acting local anesthetic effective to inhibit the disorder for greater than one hour and a persistent local anesthetic effective to inhibit the disorder for greater than two hours.

10. The method of claim 1, wherein the local anesthetic is selected from the group consisting of ambucaine, amolanone, amylocaine, benoxinate, betoxycaine, biphenamine, bupivacaine, levo-bupivacaine, butacaine, butamben, butanilicicaine, butethamine, butoxycaine, carticaine, cocaethylene, cyclomethycaine, dibucaine, dimethisoquin, dimethocaine, diperodon, dyclonine, ecgonidine, ecgonine, ethyl aminobenzoate, ethyl chloride, levo-etidocaine, etidocaine, dextro-etidocaine, β-eucaine, euprocin, fenalcomine, fomocaine, hexylcaine, hydroxyprocaine, hydroxytetracaine, isobutyl p-aminobenzoate, leucinocaine mesylate, levoxadrol, meperidine, levo-mepivacaine, mepivacaine, meprylcaine, metabutoxycaine, methyl chloride, myrtecaine, naepaine, octacaine, orthocaine, oxethazaine, parethoxycaine, phenacaine, phenol, a pipecoloxylidide, piperocaine, piridocaine, polidocanol, pramoxine, sameridine, prilocaine, propanocaine, proparacaine, propipocaine, propoxycaine, pseudococaine, pyrrocaine, quinine urea, risocaine, ropivacaine, levo-ropivacaine, salicyl alcohol, tetracaine, tolycaine, trimecaine, veratridine, zolamine, a 2-alkyl-2-alkylamino-2',6'-acetoxylidide compound, a glycerol 1,2-bis-aminoalkyl ether compound, a benzisoxazole compound, an O-aminoalkylsalicylate compound, a heterocyclic phenoxyamine compound, a 2-substituted imidazo(1, 2-A)pyridine compound, a 3-aryl substituted imidazo(1,2-A)pyridine compound, a polyorganophosphazene compound, a tertiary-alkylamino-lower acyl-xylidide compound, an amidinourea compound, a 3-(5'-adenylate) of a lincomycin compound, a 3-(5'-adenylate) of a clindamycin compound, an N-substituted derivative of a 1-(4'-alkylsulfonylphenyl)-2-amino-1,3-propanediol compound, a tertiary aminoalkoxyphenyl ether compound, an adenosine compound, adenosine, adenosine monophosphate, adenosine diphosphate, or adenosine triphosphate, a lauryl polyglycol ether compound, a 2-(ω-alkylaminoalkyl)-3-(4-substituted-benzylidene) phthalimidine compound, a 2-(ω-dialkylaminoalkyl)-3-(4-substituted-benzylidene) phthalimidine compound, an N,N,N-triethyl-N-alkyl ammonium salt, an L-N-n-propylpipecolic acid-2,6-xylidide compound, a polymer comprising repeating units of one or more local anesthetic moieties, an N-substituted 4-piperidinecarboxamide compound, an N-substituted 4-phenyl-4-piperidinecarboxamide compound, a compound of formula I, and a compound of formula II; and a pharmaceutically acceptable derivative thereof.

11. The method of claim 1, wherein the long-acting local anesthetic is selected from the group consisting of bupivacaine, levo-bupivacaine, ropivacaine, levo-ropivacaine, tetracaine, etidocaine, levo-etidocaine, dextro-etidocaine, levo-mepivacaine, and a pharmaceutically acceptable derivative thereof.

12. The method of claim 11, wherein the long-acting local anesthetic is ropivacaine.

13. The method of claim 11, wherein the long-acting local anesthetic is levo-ropivacaine.

14. The method of claim 11, wherein the long-acting local anesthetic is bupivacaine.

15. The method of claim 11, wherein the long-acting local anesthetic is levo-bupivacaine.

16. The method of claim 1, wherein the composition comprises a eutectic mixture of at least one long-acting local anesthetic and another local anesthetic.

17. The method of claim 1, wherein the long-acting local anesthetic is present in the composition at a concentration of about 0.01% to about 53% by weight.

18. The method of claim 1, wherein the long-acting local anesthetic is administered to the patient at a dose in an amount of about 10 micrograms to about 2.5 grams.

19. The method of claim 1, wherein the composition is administered in a unit dosage form comprising an amount of the local anesthetic of about 10 micrograms to about 2.5 grams.

20. The method of claim 1, wherein the composition is in a form selected from the group consisting of jelly, creme, gel, semi-solid, emulsion, sol-gel, foam, eutectic mixture of at least two local anesthetics, thermoreversible gel, and fluid which exhibits an increase in viscosity in a human nasal cavity.

21. The method of claim 1, wherein the composition is administered to the patient following the onset of a prodromal symptom of the disorder in the patient.

22. The method of claim 1 wherein the composition further comprises at least one additional local anesthetic.

23. The method of claim 22 wherein the at least one additional local anesthetic is selected from the group consisting of lidocaine, lidocaine salicylate monohydrate, cocaine, procaine, and 2-chloroprocaine.

24. A method of inhibiting a muscular headache in a human patient, the method comprising dorsonasally administering to the patient over a period of time of less than about one half hour a composition comprising a long-acting local anesthetic comprising a long-acting local anesthetic other than 2-(diethylamino)-N-(2,6dimethylphenyl)acetamide or cocaine in an amount effective to anesthetize a dorsonasal nerve structure, whereby anesthetizing the dorsonasal nerve structure is effective, following completion of the administration of the composition, to inhibit the muscular headache for greater than one hour.

* * * * *